United States Patent [19]

Zdeb et al.

[11] Patent Number: 4,874,366
[45] Date of Patent: Oct. 17, 1989

[54] HOUSING ENABLING PASSIVE MIXING OF A BENEFICIAL AGENT WITH A DILUENT

[75] Inventors: Brian Zdeb, Round Lake Park; Steve Pearson; Glenn L. Slater, both of Ingleside, all of Ill.

[73] Assignee: Baxter Internatiional Inc., Deerfield, Ill.

[21] Appl. No.: 287,504

[22] Filed: Dec. 19, 1988

Related U.S. Application Data

[63] Continuation of Ser. No. 154,523, Feb. 7, 1988, abandoned, which is a continuation of Ser. No. 721,991, Dec. 3, 1984, abandoned.

[51] Int. Cl.$^4$ .................................... A61M 5/00
[52] U.S. Cl. .................................... 604/56; 604/85
[58] Field of Search ............................ 604/56, 80–86

[56] References Cited

U.S. PATENT DOCUMENTS

| | | | |
|---|---|---|---|
| 1,655,664 | 1/1928 | Russell | 604/85 |
| 2,612,160 | 9/1952 | Barr | 604/406 |
| 3,208,639 | 9/1965 | Marwell et al. | 222/82 |
| 3,845,480 | 10/1974 | Steinberg | 340/236 |
| 3,921,636 | 11/1975 | Zaffaroni | 128/260 |
| 3,923,939 | 12/1975 | Baker et al. | 264/49 |
| 3,941,171 | 3/1976 | Ogle | 141/309 |
| 3,993,066 | 11/1976 | Virag | 604/86 X |
| 4,093,708 | 6/1978 | Zaffaroni et al. | 424/15 |
| 4,351,900 | 9/1982 | Lemonnier | 435/31 |
| 4,392,851 | 7/1983 | Elias | 604/416 X |
| 4,410,321 | 10/1983 | Pearson et al. | 604/56 |
| 4,411,662 | 10/1983 | Pearson | 604/411 |
| 4,424,056 | 1/1984 | Urquhart et al. | 604/56 |
| 4,432,755 | 2/1984 | Pearson | 604/56 |
| 4,432,756 | 2/1984 | Urquhart et al. | 604/80 |
| 4,439,183 | 3/1984 | Theeuwes | 604/85 |
| 4,458,733 | 7/1984 | Lyons | 141/1 |
| 4,465,471 | 8/1984 | Harris et al. | 604/56 |
| 4,474,574 | 10/1984 | Wolfe et al. | 604/85 |
| 4,479,793 | 10/1984 | Urquhart et al. | 604/85 |
| 4,484,909 | 11/1984 | Urquhart et al. | 604/82 |
| 4,511,352 | 4/1985 | Theeuwest et al. | 604/56 |
| 4,511,353 | 4/1985 | Theeuwes | 604/85 |
| 4,533,348 | 8/1985 | Wolfe et al. | 604/85 |
| 4,534,757 | 8/1985 | Geller | 604/85 |
| 4,534,758 | 8/1985 | Akers et al. | 604/85 |
| 4,548,598 | 10/1985 | Theeuwes | 604/85 |
| 4,552,555 | 11/1985 | Theeuwes | 604/56 |
| 4,573,967 | 3/1986 | Hargrove et al. | 604/92 X |
| 4,589,867 | 5/1986 | Israel | 604/85 |
| 4,623,334 | 11/1986 | Riddell | 604/85 |

FOREIGN PATENT DOCUMENTS

| | | |
|---|---|---|
| 1173795 | 7/1982 | Canada . |
| EP0059694 | 9/1982 | European Pat. Off. ............ 604/84 |
| 966701 | 7/1949 | Fed. Rep. of Germany . |
| 2006010 | 12/1969 | France . |

OTHER PUBLICATIONS

U.S. patent application Ser. No. 721,999; Entitled "Drug Delivery Apparatus Preventing Local and Systemic Toxicity"; Inventors.
Thomas E. Needham et al.; Filed: 12/3/84.

*Primary Examiner*—Dalton L. Truluck
*Attorney, Agent, or Firm*—Paul E. Schaafsma; Bradford R. L. Price; Paul C. Flattery

[57] ABSTRACT

A housing is provided for insertion in an intravenous delivery system including a fluid source and a fluid conduit. The housing is adapted for receiving a beneficial agent to be mixed with fluid flowing through the fluid conduit. The beneficial agent is reconstituted within the housing, eliminating the need for manual reconstitution. The housing may comprise a separate receptacle and cartridge in which the receptacle is manufactured "in-line" in an administration set and the cartridge is adapted for receiving a beneficial agent. In one embodiment of the invention, the cartridge is a standard drug vial.

41 Claims, 9 Drawing Sheets

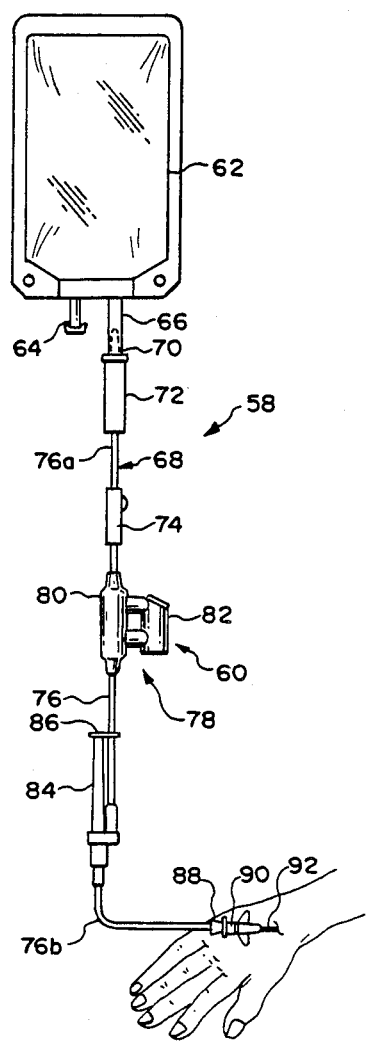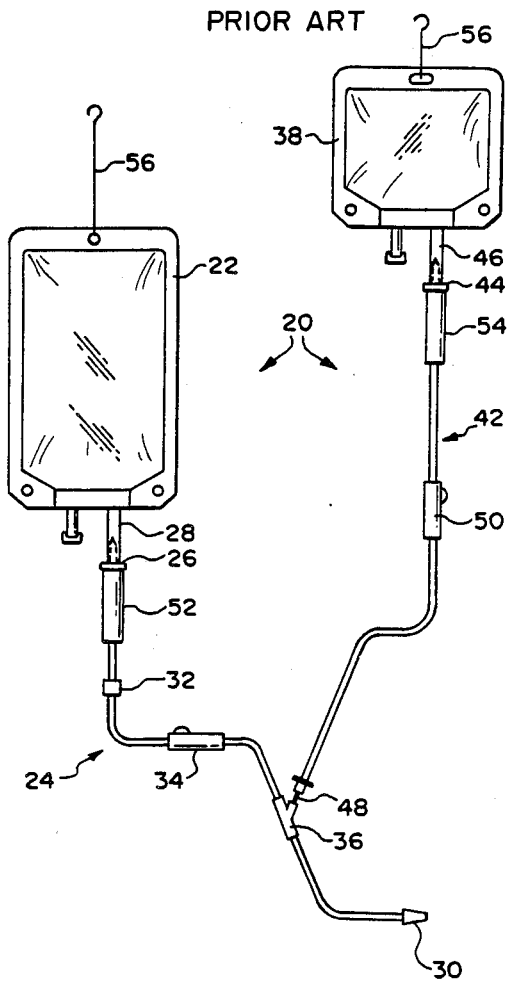

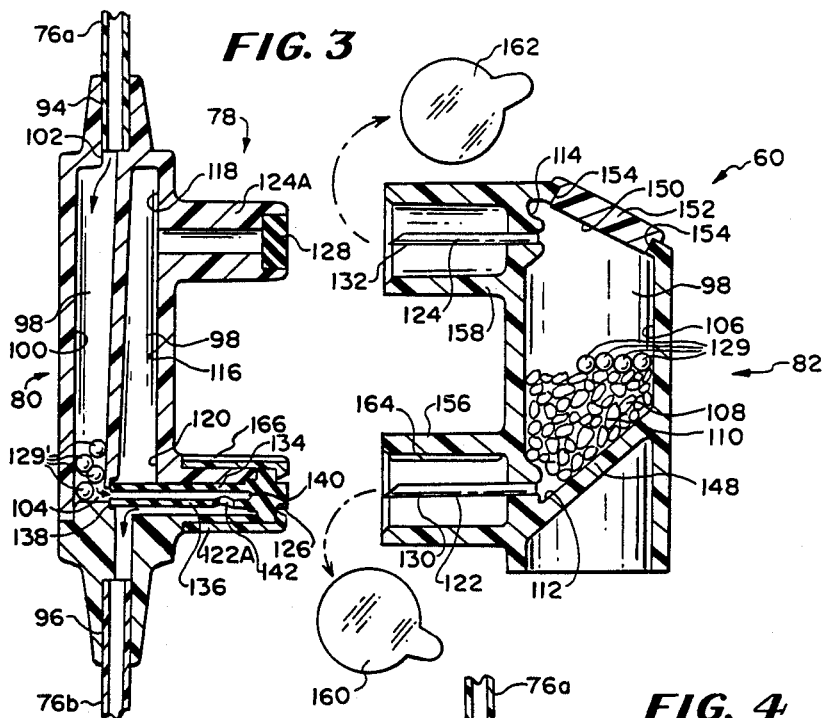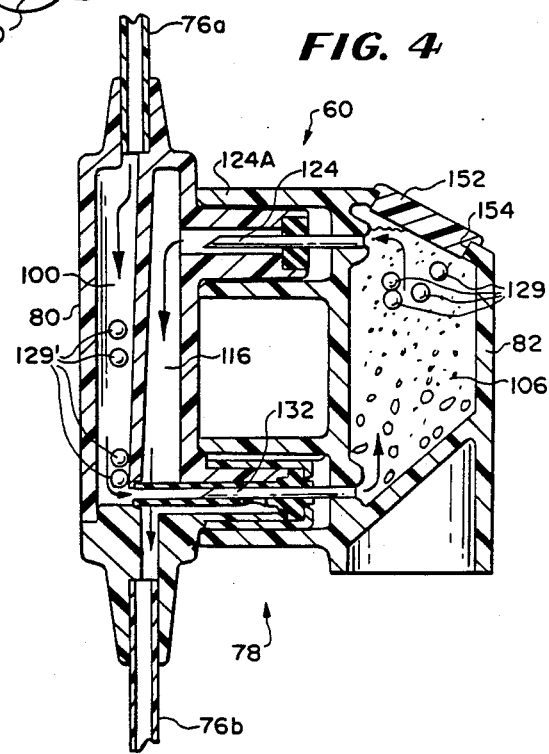

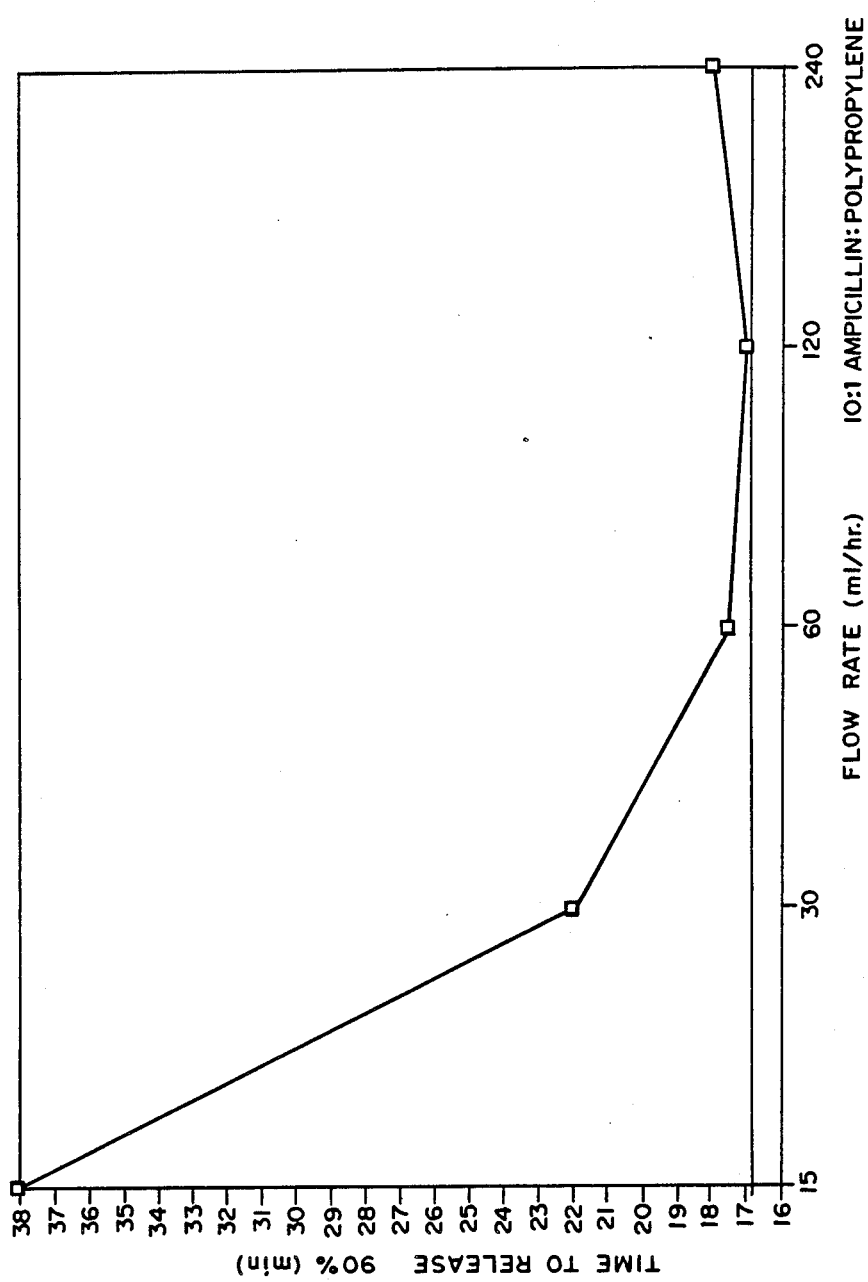

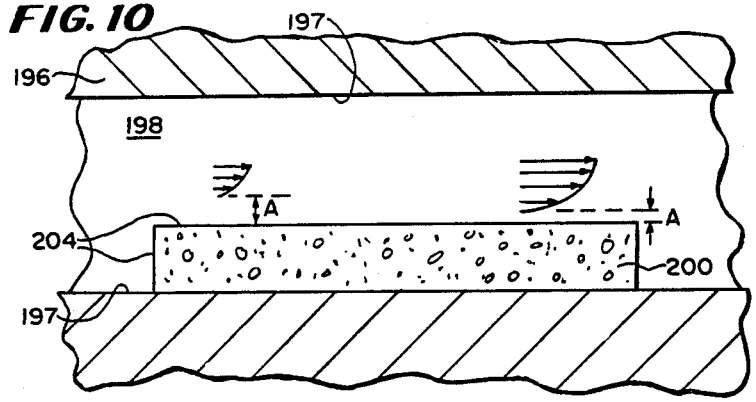
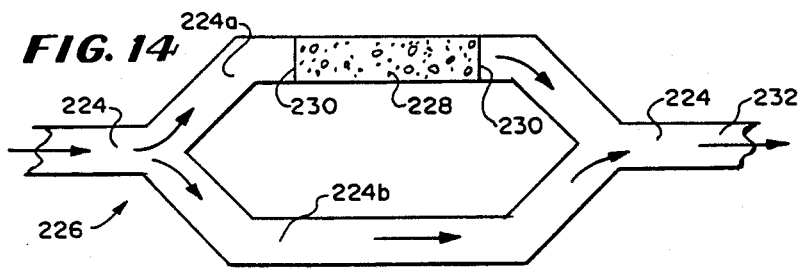
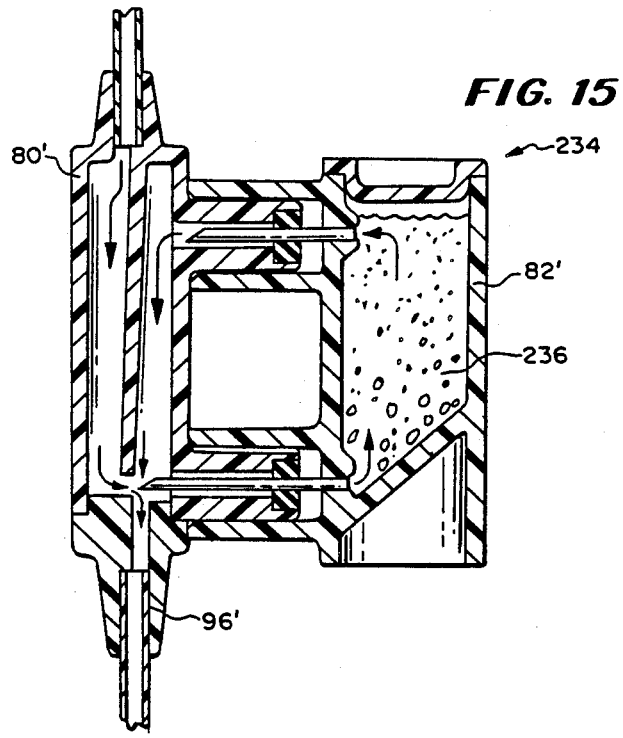

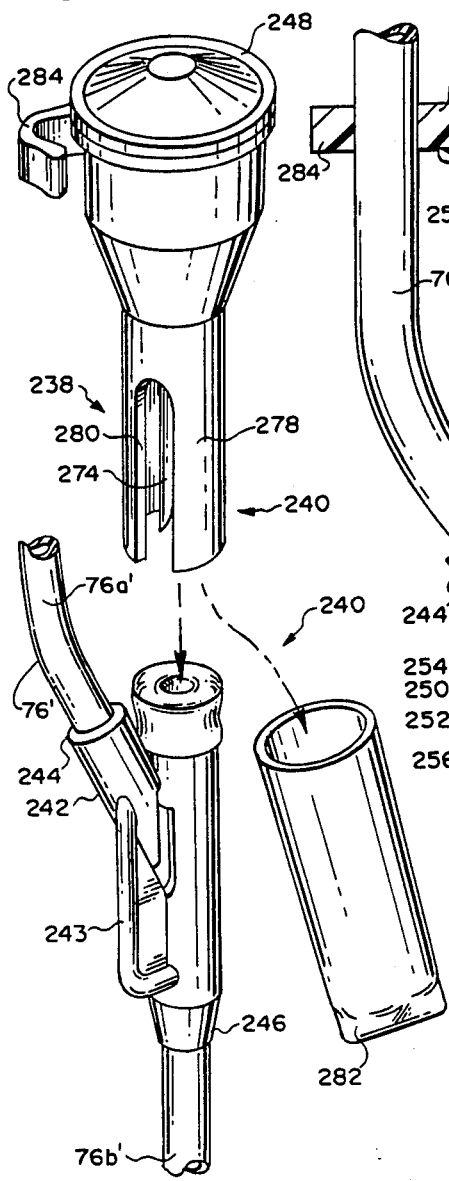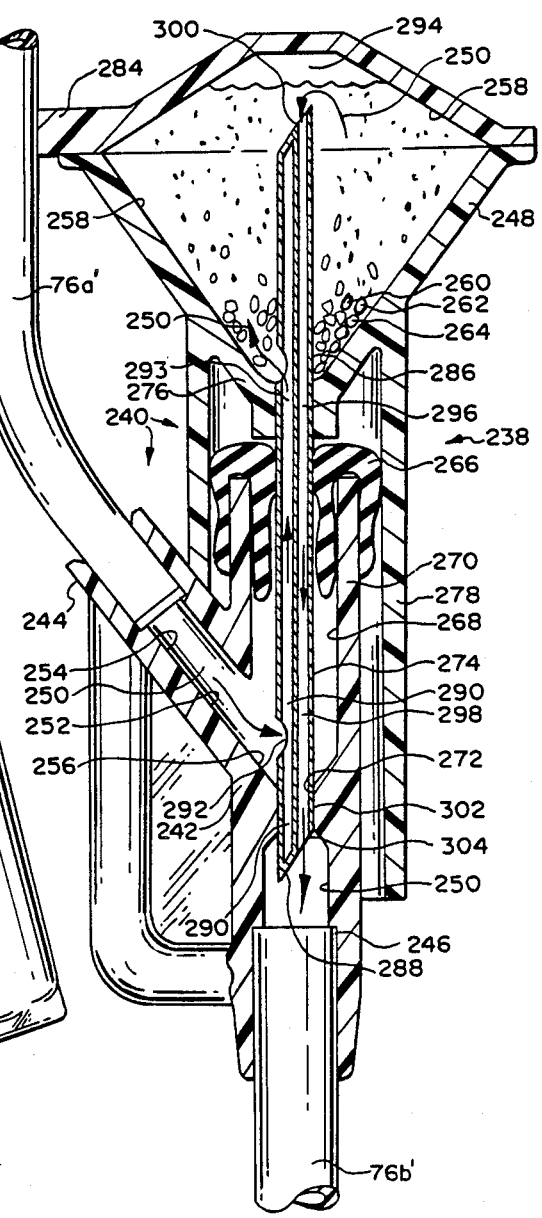

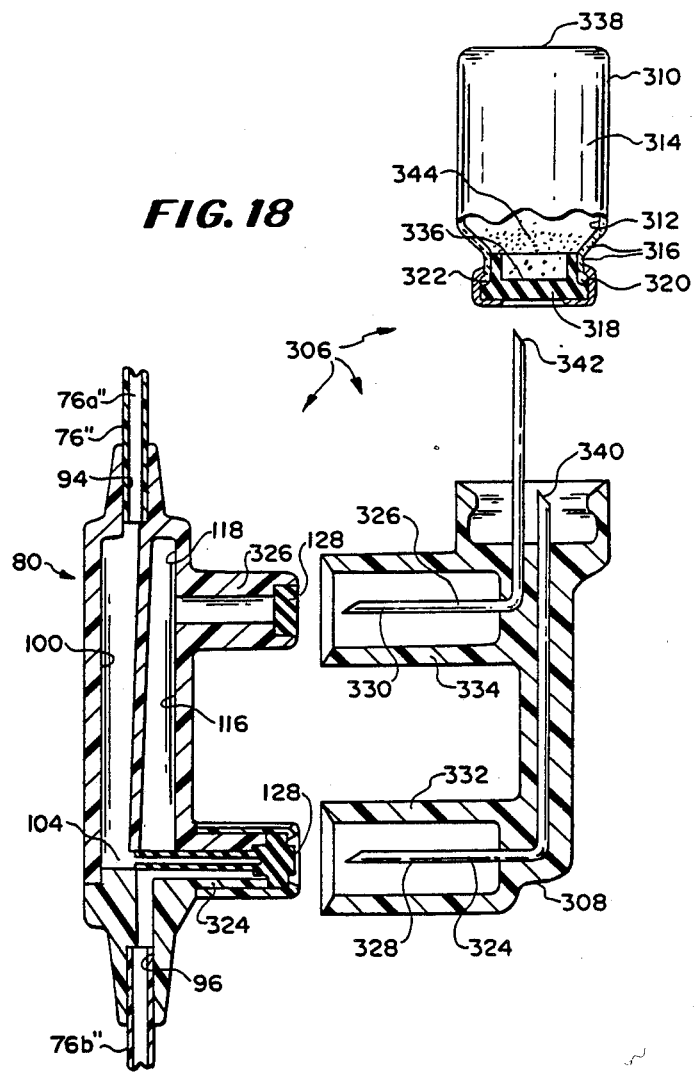

HOUSING ENABLING PASSIVE MIXING OF A BENEFICIAL AGENT WITH A DILUENT

This application is a continuation of application Ser. No. 154,423, filed Feb. 7, 1988, which is a continuation of application Ser. No. 721,991 filed Dec. 3, 1984, both now abandoned. There is an application filed concurrently herewith, entitled "Drug Delivery Apparatus Preventing Local and Systemic Toxicity" filed in the name of Thomas E. Needham et al., U.S. Patent application Ser. No. 721,999, assigned to the assignee of the present invention.

TECHNICAL FIELD OF THE INVENTION

The present invention is related to the delivery of a beneficial agent to a patient and is more particularly directed to the passive delivery of a drug to the intravenous system of a patient in a safe and effective manner.

Background of the Invention

Many drugs are mixed with a diluent before being delivered intravenously to a patient. The diluent may be, for example, a dextrose solution, a saline solution or even water. Many such drugs are supplied in powder form and packaged in glass vials. Other drugs, such as some used in chemotherapy, are packaged in glass vials in a liquid state.

Powdered drugs may be reconstituted in a well known manner, utilizing a syringe which is used to inject liquid into the vial for mixing, the syringe eventually withdrawing the mixed solution from the vial. When a drug must be diluted before delivery to a patient the drug is often injected into a container of diluent after it is reconstituted, where the container may be connected to an administration set for delivery to a patient. More specifically, the diluent is often packaged in glass bottles, or flexible plastic containers such as are sold under the names MINI-BAG ™ AND VIA-FLEX ® by Travenol Laboratories, Inc. of Deerfield, Ill. These containers have administration ports for connection to an administration set which delivers the container contents from the container to the patient. The drug is typically added to the container through an injection site on the container Drugs may be packaged separately from the diluent for various reasons. One of the most important reasons is that many drugs do not retain their chemical and physical stability when mixed with a diluent and thus cannot be stored for any substantial period of time. Also, drugs are often packaged separately from the diluent because many firms which manufacture drugs are not engaged in the business of providing medical fluids in containers for intravenous delivery, and vice versa.

Therefore, a doctor, nurse, pharmacist or other medical personnel must mix the drug and diluent. This presents a number of problems. The reconstitution procedure is time consuming and requires aseptic technique. The operator must provide the proper diluent and a syringe before beginning. Often the powdered drug is "caked" at the bottom of the vial. Thus, when liquid is injected into the vial from a syringe the surface area of contact between the liquid and the powdered drug may be quite small initially, thus making the mixing procedure even more time consuming. Because of the limited vial volume, the increasing drug concentration in the diluent makes it harder to finish the reconstitution process. The operator may attempt to solve this by repeatedly injecting solution into the vial, mixing and withdrawing the solution but this makes necessary additional injections and movement of the syringe which increase the likelihood of contamination. Also, it is sometimes difficult to get all of the drug and/or liquid out of the vial, thus increasing the time required to perform the reconstitution procedure.

The reconstitution procedure should be performed under preferably sterile conditions. In addition to such a requirement making the operator justifiably more cautious and consuming more time, sterile conditions are often hard to maintain. In some instances, a laminar flow hood may be required under which the reconstitution procedure is performed.

Some drugs, such as some chemotherapy drugs, are toxic. Exposure of the operator to the drugs during reconstitution may be dangerous, especially if the operator works with such drugs on a daily basis and is repeatedly exposed to them.

A further problem is that the reconstitution procedure provides a source of confusion as to which container contains which drug. The diluent container should be marked with the drug with which it has been injected and the name of the patient to whom it should be delivered.

After a drug is reconstituted and withdrawn into a syringe barrel, the drug may in some instances be injected immediately into the intravenous system of a patient. More typically however, the reconstituted drug is injected from the syringe into a larger container of solution as discussed above, for connection to an intravenous administration set. This is because often the drug reconstituted in the syringe is still at a concentration so high as to cause local toxicity in the veins of a patient near the injection site where the needle pierces the skin. This may create severe vein irritation which may be medically harmful. Additionally, while the proper dose of medication is in the syringe, immediate injection into the patient's blood stream may create a condition of systemic toxicity wherein the level of drug concentration in the patient's entire blood stream is dangerously high. Yet another reason for not making the injection from the syringe directly into the patient is that it creates an additional injection site into the patient, which may be painful for the patient and provides another opportunity for infection.

For these reasons, the reconstituted drug is more typically injected into a diluent container.

A patient may typically be administered a dextrose or saline solution from a large volume parenteral container, for example, such as a one liter container, delivered through an administration set such as a CONTINU-FLO ® administration set sold by Travenol Laboratories. If the reconstituted drug were injected into the large volume parenteral container, delivery of the drug would usually be delivered over too long a time period. Often, these large volume fluids are delivered at very slow flow rates.

More typically, the reconstituted drug is injected into a small volume parenteral container, such as a fifty milliliter container sold by Travenol Laboratories. This MINIBAG ™ container is hung at a higher elevation than the large volume parenteral container and is connected by a secondary administration set to an injection site on the primary administration set. Because it is maintained at a higher elevation, the reconstituted drug in the small volume container is delivered, after which fluid from the large volume container begins to flow once more.

A closed reconstitution delivery system is disclosed in U.S. Pat. Nos. 4,410,321; 4,411,662; 4,432,755; and 4,458,733, all assigned to Baxter Travenol Laboratories Inc., the assignee of the present invention. As shown therein, a container includes a drug and a diluent in separate compartments which are reconstituted in a closed system before the drug is delivered to the patient. Typically, the container is connected to an administration set which is connected at its other end to the primary administration set, such as with the small volume parenteral container described above. The container shown in these patents solves many of the problems associated with syringe reconstitution. The product does however necessitate a series of reconstitution steps which must be performed by the nurse or other operator prior to delivering the fluid from the container.

Delivery of a drug or other beneficial agent in a manner not requiring reconstitution steps by an operator is shown in U.S. Pat. Nos. 4,424,056; 4,432,756; 4,439,183; 4,474,574; 4,479,793; and 4,479,794 and Canadian Pat. No. 1,173,795, assigned to Alza Corporation of Palo Alto, Calif. As disclosed in those patents, a parenteral delivery system is disclosed which has a formulation chamber therein for administering a beneficial agent such as a drug. The system is advantageous in that it provides for reconstitution of the drug by fluid flowing from a large volume parenteral container for example, through the administration set containing the formulation chamber with the drug therein. The system intends to eliminate the need for the time consuming reconstitution procedure described above and appears to eliminate the problems associated with the reconstitution procedure.

Another passive reconstitution system is disclosed in European Patent Application No. 0059694 to Aktiebolaget Hassle of Sweden.

Still another device for delivering a drug "in-line", i.e., in the administration set, is disclosed in Australian Patent No. 15762/83 and corresponding European Patent Application No. 0100296, assigned to Ciba Geigy AG of Switzerland. The device holds the drug and includes a section through which the liquid passes in a direction substantially opposite to the general direction in which liquid flows to the patient.

Yet another system which attempts to provide for drug reconstitution in-line without manual reconstitution by a nurse or other operator is shown in U.S. Pat. No. 4,465,471, assigned to Eli Lilly and Co. of Indianapolis, Ind. That patent discloses constructions for a receptacle in the administration set itself. A separate cartridge containing the drug to be reconstituted and delivered to the patient is plugged into the receptacle.

All the publications described above are directed to solutions to the time consuming reconstitution procedure and its associated problems. In most of the offered solutions, delivery of the drug is intended to be passive, i.e., once the drug is placed into the administration set, manual reconstitution steps are not required.

Still another common feature of the attempted solutions disclosed in these publications, except for U.S. Pat. Nos. 4,410,321; 4,411,662; 4,432,755; and 4,458,733 is that delivery of the drug is intended to be able to be made in a manner which is essentially independent of the fluid flow rate through the administration set and into the patient. Stated differently, the systems are designed to deliver a certain dosage of drug in a preselected time period, within a broad range of fluid flow rates. Delivery of a drug independent of flow rate is desirable because it ensures that the necessary dosage will be delivered within a therapeutically acceptable time period, which may be typically about twenty to thirty minutes, although this time period may vary depending upon the drug and dosage.

By making delivery of the drug or other beneficial agent independent of the flow rate, the system ensures that the drug will not be delivered too quickly should the flow rate be set too high by the nurse or other operator, thereby preventing the problem of systemic toxicity discussed above.

Some of the documents, such as U.S. Pat. Nos. 4,424,056; 4,479,793; and 4,479,794, are also directed to systems having a beneficial agent placed "in-line" in an administration set for mixing of the agent and delivery to a patient, wherein the delivery of the agent may be made in a given volume of fluid. Also, a valve controlling fluid flow may be manually operated to deliver the agent in a manner which can be made dependent upon fluid flow.

It is believed that all of the automatic reconstitution type systems suffer from a critical disadvantage which does not take into account typical conditions in a hospital setting. The critical disadvantage is that at low flow rates, there is a danger that the concentration of drug in the fluid being delivered to the patient will become dangerously high, resulting in local toxicity to the patient near the point of introduction into the body.

Nurses typically work with heavy work loads and need to react quickly to emergency situations. It is possible that a nurse setting up one of the passive type delivery systems mentioned above would need to leave the patient to respond to an emergency elsewhere. The nurse may attempt to keep the "status quo" by turning off fluid flow or turning it very low before rushing away from the patient's bed side. Alternatively, the nurse may forget to set an adequately high flow rate. Yet another possibility is that the flow rate may decrease over time as the fluid is being delivered to the patient because of, for example, changes in the administration set tubing lumen as restricted by a controller such as a roller clamp, over time, or changes to the system caused by movement of the patient or the delivery system or both.

It is believed that the possibility of a situation existing with a low flow rate in a passive type drug reconstitution system is significant. It is further believed that the resulting harm to the patient may be severe.

Another disadvantage of some of the passive type drug delivery systems is that they require the chamber or housing for the drug or other beneficial agent to be incorporated into the administration set so that the drug must be sold as a unit with the administration set. Such an arrangement is medically impractical and commercially unfeasible because it necessitates that a hospital keep a large inventory of sets, according to type of drug and dosage. The hospital purchase agent must anticipate usage of various types of drugs in addition to anticipating usage of various types of administration sets. Furthermore, such an arrangement necessitates changing the set every time it is desired to deliver a dose of a beneficial agent, greatly raising hospital costs for sets, requiring significant additional nursing time, increasing the chances of infection and disturbing the patient. For example, if four doses were required per day, four different administration sets would be required, whereas a typical administration set might be used for twenty-four to perhaps forty-eight hours. Such an arrangement also raises difficult problems of keeping the drug in an environment separate from moisture and air during storage, which may have a deleterious effect on drug efficacy.

Known cartridge type systems may solve the problems associated with an in-line drug system, but may suffer from the need for temporarily disconnecting the administration set delivering the drug to incorporate the housing having the drug therein within the delivery system.

Existing cartridge type device designs may suffer from other drawbacks, such as the need for an air eliminating device within the cartridge to permit the device to operate, thereby raising the cost of the cartridge; the need for a liquid-pervious barrier to the dry medicine in the cartridge; or the existence of flow patterns which do not appear to effectuate the efficient delivery of a large percentage of the drug dosage in the required time period.

Most existing cartridge device designs do not direct all fluid flow through the cartridge, which results in a more complicated delivery system that is harder to control with different drugs and may require more than one receptacle configuration depending on the kind of drug in the inserted cartridge.

Existing cartridge device designs do not provide for fluid flow around all the beneficial agent in the cartridge from the beginning of fluid flow therethrough, resulting in inconsistent mixing over time.

Existing cartridge device designs do not include means for preventing insertion of the cartridge into the receptacle in an improper manner and do not include any visual indicator that the drug dose has been mixed and delivered downstream.

SUMMARY OF THE INVENTION

The present invention eliminates the time consuming manual steps required for reconstitution of a drug or other beneficial agent. This passive mixing of the beneficial agent is achieved by providing a housing which may be inserted into an intravenous delivery system including a fluid source and a fluid conduit, wherein fluid is delivered from the fluid source through the conduit to the intravenous system of a patient. The housing is adapted for receiving a beneficial agent to be mixed with fluid flowing through the fluid conduit. In the preferred embodiments of the invention, the housing includes a separate receptacle and cartridge. The receptacle is placed "in-line" in an intravenous administration set during manufacture of the set. The cartridge may include the beneficial agent as delivered to the hospital or other medical facility or alternatively, the hospital pharmacist or other personnel may fill the cartridge with a beneficial agent.

In the preferred embodiments, when the cartridge, including a chamber having the beneficial agent therein, is plugged into the receptacle for fluid communication with the receptacle, virtually all fluid which flows out of the housing outlet flows through the chamber.

In the preferred embodiments the housing is designed such that fluid flow through at least a portion of the cartridge chamber is in a direction generally opposite to the direction of fluid flow from the fluid source to the patient. In the preferred embodiments fluid flow through this portion of the chamber is in a generally upward direction.

The housing of the present invention is easily primed and need not include any air eliminating device within the housing to permit air entrained in the fluid conduit to exit the housing, thus reducing the cost of the housing, particularly the cartridge.

The housing of the present invention provides for mixing of a therapeutically acceptable dose of the beneficial agent quickly enough to be within a medically acceptable time period such as about thirty minutes for example.

In one embodiment of the invention the housing includes a standard drug vial as the housing cartridge. A third, separate, intermediate portion is provided for establishing fluid flow between the cartridge and the remainder of the housing.

In one embodiment of the invention, the "in-line" receptacle includes a fluid inlet, a receiving segment, a discharge segment and an outlet, such that fluid need not enter the discharge segment to reach the outlet when the cartridge is not plugged into the receptacle.

The receptacle may include a unique flow director including a resilient tube with a flow-bypass opening therein, such that when the cartridge is not plugged into the receptacle fluid entering the receptacle flows through the resilient flow director, out the flow-bypass opening and through the outlet. When the separate cartridge is plugged into the receptacle, the resilient tubular portion of the flow director seals around the outer periphery of a cartridge cannula inserted therein so that virtually all fluid entering the receptacle flows sequentially through the receiving segment, the flow director tube, the cartridge cannula, the cartridge chamber, the discharge segment and the outlet, the receptacle being virtually devoid of fluid flow through the flow director flow bypass opening. In the preferred embodiment, the flow director intercepts but does not occlude the discharge segment in the housing.

Connecting means are provided between the separate receptacle and cartridge and may include first and second cross-over segments. The first cross-over segment is disposed between and adapted for providing fluid communication between the downstream end of the receiving segment and the upstream end of the chamber. The second cross-over segment is disposed between and adapted for fluid communication between the downstream end of the chamber and the outlet, and more particularly between the downstream end of the chamber and the upstream end of the discharge segment.

Puncturable means such as injection sites may be included in the cross-over segments, such as in the portions of the cross-over segments disposed within the receptacle. Puncturing means are included, such as cannulas in the cartridge portions of the first and second cross-over segments, adapted for puncturing the injection sites. The above-described flow director may include one of the injection sites.

It is preferred that the cartridge chamber upstream portion include a funnel-like configuration, widening in the downstream direction in order to provide for better mixing between the fluid and the beneficial agent within the chamber.

The invention is also directed to a housing including a visual indicator of complete mixing of the beneficial agent, such as provided by a floating sphere or spheres within the housing.

The cartridge of the housing of the present invention may include key-way means to prevent improper insertion into the receptacle.

The present invention is also directed to a cartridge for introducing a beneficial agent into an intravenous delivery system. In one embodiment, the cartridge includes two cannulas for establishing fluid flow with the fluid conduit by piercing two injection sites in the fluid conduit. When the cartridge is connected to the fluid conduit, virtually all fluid flowing in the conduit flows sequentially through a first cartridge cannula, the cartridge chamber, a second cartridge cannula and then back into the fluid conduit.

The present invention is also directed to a method of mixing a beneficial agent with a fluid.

DESCRIPTION OF THE DRAWINGS

FIG. 1 is a plan view of an intravenous delivery system including a fluid source and a fluid conduit, including the apparatus of the present invention;

FIG. 2 is a plan view of a prior art drug delivery system, utilizing large and small volume parenteral solution containers maintained at different elevations;

FIG. 3 is a cross-sectional view of a housing, including a receptacle "in-line" in an administration set and a separate cartridge adapted for receiving a beneficial agent;

FIG. 4 is a cross-sectional view of the housing illustrated in FIG. 3, but illustrating the cartridge as secured to the receptacle;

FIG. 5 is a graph tracking time of release of a beneficial agent as a function of fluid flow rate with certain control means, illustrating the fluid flow rate transition region and the first and second delivery modes;

FIG. 10 is a schematic, cross-sectional view illustrating local velocity profiles and a diffusional boundary layers;

FIG. 14 is a schematic, cross-sectional view illustrating a split fluid pathway with parallel flow segments, with a beneficial agent in one of these fluid segments;

FIG. 15 is a cross-sectional view of a housing similar to the housing illustrated in FIGS. 3 and 4, but without the flow director, and with split-flow, parallel flow segments;

FIG. 16 is a perspective view of another housing;

FIG. 17 is a cross-sectional view of the housing illustrated in FIG. 16;

FIG. 18 is a cross-sectional view of still another housing, including an "in-line" receptacle, a separate intermediate portion and a separate cartridge adapted for receiving a beneficial agent.

DETAILED DESCRIPTION OF EXAMPLES EMBODYING THE BEST MODE OF THE INVENTION

Figure 6:
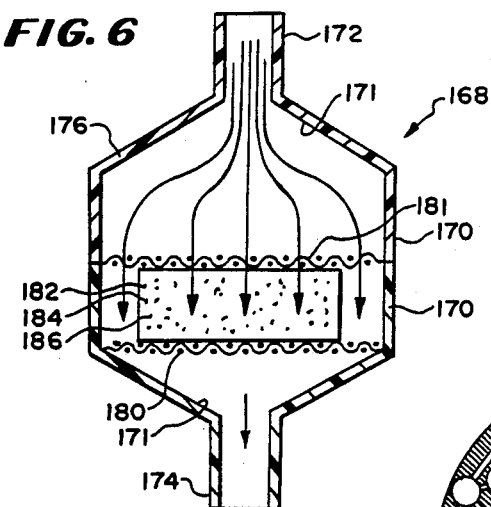
FIG. 6 is a cross-sectional view illustrating an alternate housing, used to generate the data shown in FIG. 5.

Referring to FIG. 2, there is disclosed a prior art intravenous delivery system 20 including a first fluid source such as a first fluid container 22 having a liquid therein such as water, a dextrose solution or saline solution for example. A first administration set 24 is connected by a first set spike connector 26 at its proximal end to a first container administration port 28 on the first container 22, and by a first set Luer connector 30 to a catheter 31 which enters the patient's intravenous system through the skin.

The first administration set 24 includes a check valve 32, a first flow regulating means such as a first set roller clamp 34 and a "Y" adapter injection site 36. The prior art intravenous delivery system 20 further includes a second fluid source such as a second fluid container 38 which contains a diluent such as sterile water, dextrose, or saline solution for example. A reconstituted drug may be injected into the second fluid container 38 by means of the second container injection site 40.

A second administration set 42 is connected by means of a second set spike connector 44 at its proximal end to the second container administration port 46, and by a needle 48 at its distal end to the first administration set 24 through the "Y" adapter injection site 36. The second administration set 42 includes a second flow regulating means such as a second set roller clamp 50. Each of the first and second administration sets 24, 42 includes a drip chamber 52, 54 respectively by which fluid flow through the sets 24, 42 may be determined by counting drops entering the drip chambers.

The first and second fluid containers 22, 38 may be hung by metal hangers 56 from an IV equipment pole (not shown). The second fluid container 38 is hung at a higher elevation than the first fluid container 22 so that the drug and diluent in the second container 38 will interrupt delivery of fluid in the first container 22 because of a higher head pressure. After the fluid in the second container 38 is delivered, delivery of fluid from the first container 22 to the patient resumes.

In contrast, there is shown in FIG. 1 an intravenous delivery system 58 including an apparatus 60. A fluid source such as a container 62 contains a fluid, such as sterile water, dextrose solution or saline solution for example, to be delivered to the patient. The container 62 includes an injection site 64 and an administration port 66. A fluid conduit including an administration set 68 includes a spike connector 70 at its proximal end for piercing a membrane in the administration port 66 to permit fluid to flow from the container 62 to the set 68. Downstream of the spike connector 70 is a drip chamber 72 by which a nurse or other operator may count drops per unit of time to determine the fluid flow rate through the delivery system 58. A flow regulating device such as a roller clamp 74 is disposed about plastic tubing 76 downstream of the drip chamber 72. The apparatus 60 is disposed "in-line" in the fluid conduit.

The apparatus 60 includes a housing 78. It is preferred that the housing include a receptacle 80 which is disposed in the fluid conduit tubing 76 and a separate, plug-in cartridge 82. Downstream of the housing 78 is a fluid filter 84 which may be, for example, a hollow fiber filter. The fluid filter 84 includes air eliminating means such as an air eliminating membrane 86 for eliminating air entrained in the fluid conduit. Air entrained in the fluid conduit exits the conduit into the environment through the air eliminating membrane 86.

The distal end of the administration set 68 includes a male Luer adapter 69 which connects to a catheter hub 90 of a catheter 92, which enters the patient's intravenous system through the skin.

Many other configurations of the administration set 68 for use with the apparatus 60 are possible. For example, the flow regulating means may be a separate pump into which the tubing 76 is mounted, eliminating the need for the roller clamp 74.

In this disclosure the housings and apparatus are discussed with reference to intravenous delivery systems and the intravenous system of a patient. However, the housings and apparatus may be used for the introduction of a beneficial agent into a patient at locations other than the patient's intravenous system. "Intravenous" is meant to include those other locations. The apparatus and housings are adapted for receiving a beneficial agent. "Beneficial agent" is meant to include diagnostic substances as well as substances intended to have a medically beneficial effect.

Referring now to FIGS. 3 and 4, there is illustrated the apparatus 60. The apparatus 60 includes a housing 78 which includes a receptacle 80 including an inlet 94 connected to an upstream portion 76a of the fluid conduit and an outlet 96 connected to a downstream portion 76b of the fluid conduit. The housing 78 includes a separate cartridge 82 which is plugged into the receptacle 80 to form the complete housing 78. The housing 78 may also be constructed so that the cartridge 82 and the receptacle 80 are made as a unit.

The housing 78 defines a fluid pathway 98 therethrough. The inlet 94 and the outlet 96 define part of the fluid pathway 98. The fluid pathway forms part of the fluid conduit of the intravenous delivery system 58.

The housing includes a fluid receiving segment 100 having an upstream end 102 in fluid communication with the inlet 94, and a downstream end 104. A chamber 106 adapted for receiving a beneficial agent 108 and a carrier 110 is defined by the cartridge 82. The chamber 106 defines part of the fluid pathway 98 in the housing 78. As shown in FIGS. 3 and 4, the agent and carrier are in pellet form, but other forms are also possible, as discussed below.

The chamber includes an upstream end 112 adapted for fluid communication with the receiving segment downstream end 104. The chamber also includes a chamber downstream end 114.

The housing 78 further defines a discharge segment 116 of the fluid pathway 98, including a discharge segment upstream end 118 adapted for fluid communication with the chamber downstream end 114, and a discharge segment downstream end 120 in fluid communication with the outlet 96.

The housing 78 further includes connecting means in both the receptacle 80 and the cartridge 82 for securing the cartridge to the receptacle and providing for fluid flow therebetween. The connecting means includes first and second cross-over segments 122, 124. The first cross-over segment 122 is disposed between and adapted for providing fluid communication between the receiving segment downstream end 104 and the chamber upstream end 112.

The second cross-over segment 124 is disposed between and adapted for fluid communication between the chamber downstream end 114 and the discharge segment upstream end 118. The first and second cross-over segments 122, 124 are each disposed in both the receptacle 80 and the cartridge 82.

Puncturable means are disposed in and block both the first and second cross-over segments 122, 124 in the housing 78. The puncturable means used in the housing 78 are resilient, rubber-like injection sites 126, 128 disposed in the first and second cross-over segments 122, 124 respectively. The injection sites are mounted at the ends of the receptacle portions of the first and second cross-over segments and form part of the connecting means between the cartridge and receptacle.

Puncturing means are provided in both the first and second cross-over segments 122, 124 for puncturing the puncturable means. In the housing 78, the puncturing means comprise pointed, hollow cannulas 130, 132 mounted in the cartridge portion of the first and second cross-over segments 122, 124 respectively. The cannulas 130, 132 form part of the connecting means. When the cartridge and receptacle are urged together, the cannulas 130, 132 pierce the injection sites 126, 128 respectively, thereby placing the receiving segment 100, the chamber 106 and the discharge segment 116 in fluid communication.

The first cross-over segment injection site 126 is part of a flow director 134 which is a puncturable means. In addition to the injection site 126, the flow director 134 includes a tube 136 having an upstream end 138 fluid-sealingly connected to the receiving segment downstream end 104. The injection site 126 closes the opposite end 140 of the tube 136. It is preferred that the flow director 134, including the tube 136 and the injection site 126 be made as a single piece.

The flow director 134 defines a flow bypass opening 142 in the wall of the tube 136. It is preferred that the tube 136 is resilient and sized so as to seal about the outer periphery of the cannula 130 which pierces the injection site 126, as illustrated in FIG. 4. The flow director 134 intersects but does not occlude the discharge segment 116.

Referring to FIG. 3, when the cartridge 82 is not plugged into the receptacle 80, fluid flowing from the fluid source through the fluid conduit 76 flows from the conduit upstream portion 76a, through the inlet 94 and into the receiving segment 100 of the fluid pathway 98. The fluid flows out the receiving segment downstream end 104, into the flow director 134, and then out of the flow director 134 through the flow bypass opening 142, whereupon it continues to flow out the outlet 96 into the downstream portion 76b of the plastic tubing 76.

Referring now to FIG. 4, when the chamber is in fluid communication with the receiving segment and the discharge segment, the tube 136 seals around the outer periphery of the cannula 130 so that fluid entering the flow director 134 does not exit through the flow bypass opening 142. Instead, fluid entering the flow director 134 flows through the cannula 130 into the chamber 106. The fluid continues to flow through the cannula 132, into the discharge segment 116. Fluid in the discharge 116 flows around the flow director 134, into the outlet 96 and the downstream portion 76b of the conduit. It will be seen from FIG. 4 that the direction of fluid flow through at least a portion of the chamber is in a direction generally opposite to the direction of fluid flow from the fluid source to the patient. In the housing 78, fluid flow through the chamber 106 is in a generally upward direction, which is generally opposite to the downward direction of fluid flow from the container 62 to the patient.

As fluid flows through the chamber 106, the beneficial agent 108 in the chamber 106 mixes with the fluid and is subsequently delivered therewith to the patient. As will be explained below, the beneficial agent 108 may be placed in the chamber 106 alone or combined with a dissolvable or nondissolvable carrier material 110. The beneficial agent 108 or the combined beneficial agent and carrier 108, 110 may be in pellet form as illustrated in FIGS. 3 and 4 or in a larger tablet form or in powder form with very small separate particles.

It has been found that the housing 78 permits passive drug delivery. The nurse, pharmacist or other operator need not go through a series of manual reconstitution steps. Once the cartridge 82 is plugged into the receptacle 80 and fluid begins to flow, the drug or other beneficial agent 108 is automatically mixed in with the fluid for delivery to the patient.

The upward flowpath in the chamber 106 of the housing 76 is important. Because the downstream or discharge end 114 of the chamber 106 is at the top of the chamber 106, the fluid at the downstream end 114 of the chamber has a concentration of beneficial agent 108 lower than if the downstream end of the chamber were at a lower elevation than the upstream end of the chamber. This assists in creating a housing 78 which permits delivery of the beneficial agent 108 in a manner substantially independent of the fluid flow rate so that the amount of beneficial agent 108 delivered per unit time period is substantially a constant for a given housing and beneficial agent.

Thus, the housing 78 allows for delivery of the beneficial agent 108 in a time period short enough to be therapeutically effective, such as between twenty and forty minutes. This time period is not intended to be a limitation but does represent a typically desirable delivery period for many intravenously delivered drugs. The housing 78 also prevents the drug from being delivered too quickly at high flow rates so that the medically unacceptable condition of systemic toxicity discussed above will not occur. Stated differently, the housing 78 prevents the patient's blood stream from having a dangerously high concentration of beneficial agent 108.

The upward flowpath in the chamber 106 also aids in mixing by creating swirling of the fluid as it flows upwardly through and around the beneficial agent 108. The upward flow path also assists in forcing downstream out the outlet 96 the air entrained in the housing and in the system upstream of the housing. This permits easy priming of the housing with the cartridge therein. In fact, the cartridge 82 is self-priming. Furthermore, the upward flow path in the chamber 82 of the housing 78 eliminates the need for an air vent or other air eliminating means in the cartridge 82 itself.

It is believed that air eliminating means should be included in the fluid conduit of the intravenous delivery system 58. As shown in FIG. 1, the air eliminating means may simply be the air eliminating membrane 86 of a commercially available fluid filter 84. The air eliminating means eliminates air entrained in the fluid conduit, including the housing. Although it is possible for the air eliminating membrane to be disposed within the housing, it is preferable that it be disposed downstream of the housing. By so doing, the system 58 takes advantage of the air eliminating membrane 86 already in the known fluid filter 84 which would probably be desirable in the system even without the housing. By permitting the air eliminating membrane to be external of the housing 78, and particularly external of the cartridge 82 with the chamber 106 therein, the manufacturing costs of the housing and particularly the cartridge 82 are significantly reduced.

Preferably, the chamber upstream portion adjacent the chamber upstream end 112 has a funnel-like configuration, such as the sloping upstream chamber wall 148. As seen in FIGS. 3 and 4, the funnel-like shape widens in the downstream direction. This configuration aids in the mixing process and helps to direct fluid flow around all of the beneficial agent 108, from the beginning of fluid flow through the chamber. Also preferable is a funnel like configuration adjacent the chamber downstream end 114, such as the sloping, downstream chamber wall 150 that creates a substantially funnel shape which narrows in the downstream direction. Such a structure assists in aiding fluid flow out of the chamber 106.

An additional feature of the housing 78 is a chamber plug 152 sealing a chamber access port 154. The beneficial agent 108 may be placed into the chamber 106 through the chamber access port 154. This design permits manufacture of the housing 78 with the beneficial agent 108 therein, or manufacture of a cartridge 82 which may be delivered to the hospital without a beneficial agent therein. The hospital pharmacist or the operator may then simply take out the plug, insert the beneficial agent 108 and reseal the chamber plug 152 in the access port 154, under aseptic conditions. The chamber plug 152 may be a resilient, puncturable, resealable material, to enable filling the chamber with a syringe and needle through the plug 152 in those cases where the beneficial agent is added to the cartridge 82 in the liquid state.

If the cartridge 82 is manufactured with the beneficial agent therein, the plug 152 may be sealed by means of an ultrasonic weld, solvent bonding or other permanent means. If the cartridge 82 is manufactured for addition of a beneficial agent 108 by hospital personnel, the plug 152 may be designed with a tight friction fit preventing contamination of the chamber through the access port 154 after the chamber has been resealed by the pharmacist.

Preferably, the cartridge 82 includes protective sleeves 156, 158 disposed around and spaced from the cannulas 130, 132 respectively, preventing touch contamination. The sleeves 156, 158 may be covered by removable foil tabs 160, 162 respectively, adhesively secured to the sleeves 156, 158. The tabs 160, 162 are removed before the cartridge 82 is inserted into the receptacle 80.

The protective sleeves 156, 158 also serve the important function of properly aligning the cannulas 130, 132 within the injection sites 126, 128. This is especially important for proper insertion in the flow director 134. The sleeves 156, 158 may have an inner diameter of for example about 0.005 to 0.020 inch greater than the outer diameter of the portions 122A, 124A of the first and second cross-over segments respectively on the receptacle 80. Thus, when the cartridge is plugged into the receptacle the cannula 130 will be centered in the injection site 126 so that the cannula 130 enters the inside of the tube 136 in the flow director.

An additional feature of the cartridge 82 is key way means to prevent the cartridge 82 from being secured to receptacle 80 upside down. The key way means includes a key 164 which, as illustrated in FIG. 3, is mounted on the internal wall of the sleeve 156. The key fits into a slot 166 on the portion 122A of the first cross-over segment 122 on the receptacle 80. The key way means could include many other configurations and may be disposed on the second cross-over segment 124 as well as or instead of the first cross-over segment 122. The key way means prevents the second cannula 132 from piercing the one injection site 126 and prevents the first cannula 130 from piercing the other injection site 128.

Preferably, at least a portion of the cartridge 82 is optically transparent so that the chamber 106 and the chamber contents may be clearly viewed. As will be explained further below, a carrier 110 may be placed in the chamber 106 with the beneficial agent 108. This carrier 110 may be relatively inert and not dissolvable within the fluid flowing through the cartridge 82. For this reason, it may be hard to ascertain by visual inspection whether or not the entire dose of the beneficial agent 108 has been mixed and delivered to the fluid conduit downstream of the chamber. However, visual inspection of complete dosage delivery may be a good safeguard in the intravenous system 58.

Therefore, the housing 78 includes visual inspection means which, in addition to the optically transparent cartridge portion, may also include one or more hollow plastic spheres 129 or other floating visual indicator. In the preferred embodiment, several plastic spheres 129 are carried in the chamber 106, each floating in fluids having different ranges of specific gravity. An identical set of spheres 129' are carried in the receiving segment 100. The receiving segment 100 of the receptacle 80 is also made optically transparent to view the spheres 129'. Because the beneficial agent does not enter the receiving segment 100, the number of spheres 129' floating in the receiving segment 100 will be dependent upon the specific gravity of the fluid from the fluid source.

The spheres 129' serve as a reference to determine when the agent has substantially all been mixed and delivered downstream of the chamber 106, by comparing the spheres 129 in the chamber with the spheres 129' in the receiving segment. When the same number of spheres 129, 129' remain floating in both the chamber 106 and the receiving segment 100, one knows that the specific gravities of the fluid in the chamber and the receiving segment 100 are substantially the same, so that at least almost all of the beneficial agent 108 has been transported downstream of the chamber 106. Until the agent 108, and the carrier 110 if dissolvable, leave the chamber 106 the specific gravity of the fluid in the chamber will be greater than the specific gravity of the fluid in the receiving segment, and hence more spheres 129 will be floating in the chamber than in the receiving segment.

Spheres may be disposed in the discharge segment 116 in addition to, or in place of, the spheres 129 in the chamber 106, in order to determine whether beneficial agent 108 remains in the fluid in the discharge segment or whether the agent 108 has passed downstream of the discharge segment. The discharge segment of the receptacle 78 would be optically transparent, and the spheres in the discharge segment 116 also could be compared with the spheres in the receiving segment 100.

The effect of downward flow in the receiving segment 100 on the location of the spheres 129' therein can be minimized by enlarging the volume of the receiving segment. Alternatively, the operator may, by means of the roller clamp 74 for example, momentarily stop fluid flow to compare the spheres 129, 129'.

Another embodiment of the visual indicator means is to include spheres 129 only in the chamber 106 and not in the receiving and discharge segments 100, 116. In this embodiment, the floating specific gravity range for each sphere is preselected according to the beneficial agent 108, and the carrier if dissolvable, to be carried in the chamber 106. As mixing of the agent 108 nears completion, spheres begin to drop, providing an indication that mixing is nearing completion. After mixing of the agent 108 is complete and has been delivered out the chamber 106, the last sphere 129 drops.

Still another embodiment of the visual indicator means is to include a single sphere 129 in the chamber 106, once again floating in fluids down to a preselected minimum specific gravity, depending on the agent 108, and the carrier 110 if dissolvable. In this embodiment, as fluid flows through the chamber 106 and the last portion of the beneficial agent 108 is mixed and delivered downstream, the specific gravity of the fluid in the chamber becomes less and the sphere 129 begins to fall until coming to rest adjacent the bottom, upstream portion of the chamber 106. The visual indicator is intended to show whether or not substantially the entire dose has been mixed and delivered downstream.

Preferably, the floating spheres 129, 129' are made of a material to which small air bubbles do not easily adhere, so that the floating ability of the spheres 129 are not changed thereby.

Although the housing 78 described above facilitates passive drug reconstitution and delivers drug out the outlet 96 in the manner independent of the fluid flow rate through the housing 78, the housing 78, as above-described, does not solve the medically unacceptable problem of excessively high drug concentrations near the entry point into a patient's intravenous system at low flow rates, referred to as local toxicity. This problem is associated with other known passive type drug delivery systems. Stated differently, the present apparatus 60 prevents a medically unacceptably high concentration of beneficial agent in the fluid delivered to the patient, thereby preventing serious vein irritation and any other medical problems associated with a toxic concentration of drug or other beneficial agent in the fluid entering the patient's intravenous system.

The apparatus 60 prevents local toxicity while also permitting delivery of the beneficial agent dose in a time period short enough to be medically acceptable. The apparatus 60 includes the housing 78 and means for controlling the rate of delivery of the beneficial agent out of the housing outlet 96. The control means creates two different delivery modes for the beneficial agent, depending upon the fluid flow rate out the outlet 96. The control means may include one or more of several structural features. In the apparatus 60 illustrated in FIGS. 3 and 4 for example, the control means includes pellets which include not only the beneficial agent 108 but also a carrier 110 such as a nondissolvable, porous polypropylene plastic, as will be explained in detail below.

The control means creates a first delivery mode in which the fluid velocity through the chamber 106 is high enough that the rate of delivery of the beneficial agent is substantially independent of the fluid flow rate through the chamber, providing all the advantages of flow rate independent agent delivery discussed above. Additionally, the control means also creates a second delivery mode in which the fluid velocity through the chamber is slow enough that the rate of delivery of the beneficial agent is dependent upon the fluid flow rate through the chamber. The first and second delivery modes include a fluid flow rate transition region between the higher fluid flow rates associated with the first delivery mode and the lower fluid flow rates associated with the second delivery mode. In this fluid flow rate transition region the degree of dependence of the rate of beneficial agent delivery upon the fluid flow rate changes significantly.

Stated differently, in the first delivery mode the amount of beneficial agent delivered per unit time, for example grams per minute, is substantially a constant. At lower flow rates, in the second delivery mode, the amount of beneficial agent delivered per unit time becomes a variable and decreases as the fluid flow rate decreases.

The apparatus 60, including the control means, even prevents local toxicity if fluid flow is turned off entirely for extended time periods and then resumed at a low or a high flow rate. Multiple dosing, even at low flow rates, is made possible with the apparatus 60. For example, a fraction of the agent 108 in the chamber 106 may be delivered at flow rates low enough to be operating in the second delivery mode, for a given time period. Fluid flow can subsequently be turned off or turned to a lower flow rate. Another fraction of the available agent 108 can be delivered later, in the same manner, if desired.

Referring to FIG. 5 there is shown a graph illustrating the effect of the control means. The horizontal axis of the graph indicates the fluid flow rate and the vertical axis of the graph indicates the time required to deliver ninety percent of the available beneficial agent 108. The housing, beneficial agent and carrier used to generate this data are described below. Generally, in FIG. 5, the fluid flow rate transition region is between fluid flow rates of about thirty and sixty milliliters per hour. The first delivery mode begins in the fluid flow rate transition region and runs all the way to the highest flow rate tested, 240 ml/hour. Especially at flow rates at or above 60 ml/hour, the plotted line is substantially horizontal, representing the first delivery mode where the agent delivery rate is substantially independent of fluid flow rate.

The second delivery mode begins somewhere in the fluid flow rate transition region and extends down to 15 ml per hour, the lowest flow rate tested. The plotted line in this area of the graph is steeply sloped, representing the strong dependence of the agent delivery rate upon the fluid flow rate.

FIG. 6 is a cross-sectional view of an apparatus 168 including a housing 170 having an inlet 172 and an outlet 174 adapted for connection to upstream and downstream portions of a fluid conduit, respectively. The arrows illustrate the direction of fluid flow through the apparatus 168. The housing 170 was used to generate the data shown in the graph of FIG. 5.

The housing 170 includes an upper cup 176 secured to a lower cup 178 to form a chamber 171. The chamber 171 has a central cylindrical portion having an inner diameter of abut 3/4 inch and upper and lower conical portions defined by the upper and lower cups 176, 178 respectively. A lower metal screen mesh 180 is mounted at its periphery by friction fit, for example, to the lower cup 178, at the junction between the cylindrical and lower conical portions. The remainder of the screen mesh 180 is spaced from the lower cup 178. An upper metal screen mesh 181 is mounted at its periphery between the upper and lower cups 176, 178 for example. A tablet 182 rests on the lower screen mesh 180 and is held in position by the upper screen mesh 181. The tablet 182 includes a beneficial agent 184 and a carrier 186. As used in the test procedure, only for purposes of illustration, and not intended to limit the scope of the disclosure, the tablet 182 has a diameter of 9/16 inch and contains a 500 mg dose of sodium ampicillin as the beneficial agent 184. The tablet also includes as the carrier 186 a porous polypropylene plastic. The ratio by weight of sodium ampicillin to polypropylene plastic is about 10 to 1.

Figure 7:
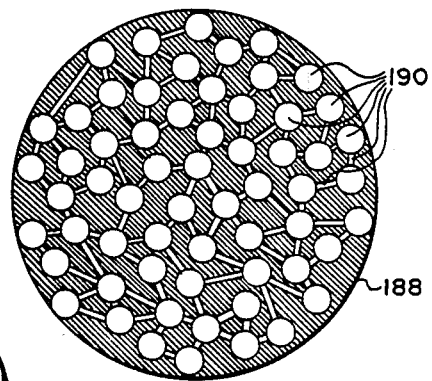
FIG. 7 is a schematic view of a porous polypropylene particle such as used to make the tablet in the housing of FIG. 6.

Before manufacture of the tablet 182, the polypropylene plastic existed in particles 188 having a mean particle size of approximately 53 microns ±10 microns, although a wide variety of particle sizes are believed to work. A plastic particle 188 is illustrated schematically in FIG. 7. The plastic supply particles 188 are porous, having interconnecting voids 190 each of which is about 7 to 10 microns in diameter. The plastic particles 188 may be as manufactured by Armak Laboratories of McCook, Ill. under the name Accurel.

Figure 8:
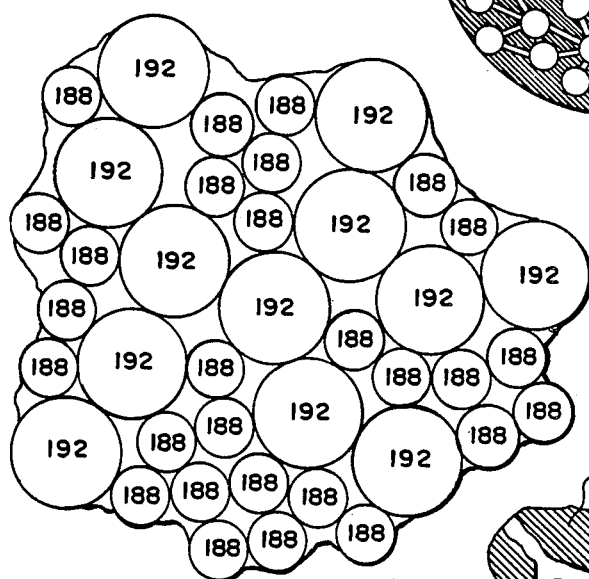
FIG. 8 is a schematic, fragmentary enlarged view of the tablet shown in the housing of FIG. 6, illustrating both the beneficial agent and the polypropylene carrier.
Figure 9:
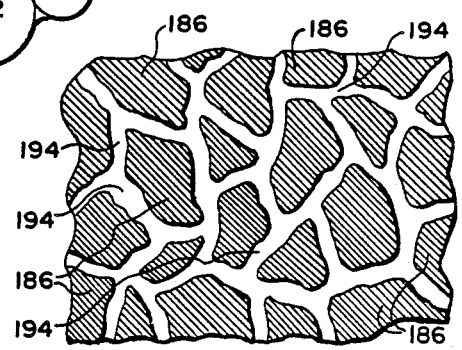
FIG. 9 is a schematic, fragmentary enlarged view of the tablet in the housing of FIG. 6, illustrating channels of beneficial agent within the polypropylene carrier.

The tablet 182 is formed by compressing the sodium ampicillin 184 and the plastic supply particles 188 with a compression force of roughly 8,000 pounds per square inch, forming a structure illustrated schematically in FIGS. 8 and 9. It is believed that during compression of the formed tablet 182, some of the defined voids 190 in the individual plastic supply particles 188 are compressed. It is believed that the structure appears such as shown in FIG. 8, with beneficial agent particles 192 mixed in with the plastic supply particles 188. Except for voids 190 on the surface of the plastic supply particles 188, it is not believed that the beneficial agent 184 enters into the defined voids 190 in the plastic particles 188.

Referring now to FIG. 9, it is believed that because there is significantly more beneficial agent 184 than carrier 186 in the tablet 182, there are therefore created channels 194 of beneficial agent 184, comprising the compressed agent particles 192.

The convoluted channels 194 of beneficial agent 184 in the tablet 182 cause the beneficial agent to be metered out of the tablet 182 at a set rate, which is typically less than the beneficial agent's inherent rate of dissolution. This set rate, independent of flow rate in the first delivery mode, is controlled by the compression force used in forming the tablet, thereby adjusting the void volume of the plastic particles 188, the void volume of the agent particles 192 and the void volume of the tablet 182. The set rate is further controlled by adjusting the surface area of the tablet, the weight ratio between the beneficial agent and the carrier, the particle size of the beneficial agent and the carrier and the shape of the tablet 182.

The greater the compression that is used in forming the tablet, the less will be the set rate. The smaller the surface area of the tablet exposed to fluid flow, the less will be the set rate. The lower the weight ratio of the beneficial agent to the carrier, the less will be the set rate. It is important to remember that the set rate is not an absolutely precise value, but that the set rate does not vary substantially above a certain flow rate, such as 60 ml/hour in the FIG. 5 example.

As illustrated in FIG. 6, fluid flowing through the housing 170 passes over the exterior surface of the tablet 182. Another flow arrangement is illustrated in FIG. 10, wherein there is shown a housing 196 defining a fluid pathway 198 in which is disposed a tablet 200 of a beneficial agent and a carrier. Fluid flow is from left to right in FIG. 10, which illustrates schematically what also happens in the apparatus 168 shown in FIG. 6. The tablets 182 and 200 permit the housings 170, 196 to utilize mass transfer concepts for producing a second delivery mode wherein the delivery rate of the beneficial agent is dependent upon the fluid flow rate.

The tablets 182, 200 present a mass transfer resistance to transport of the beneficial agent from the interior of the tablet to the surface of the tablet. This means the set delivery rate is less than the inherent rate of dissolution of the beneficial agent, as described above. Also, an additional resistance to mass transfer is presented by the diffusional boundary layer that exists from the surface 202, 204 of each of the tablets 182, 200 respectively out a short distance "A" into the flowing fluid. The rate of mass transfer of the beneficial agent 184 through this diffusional boundary layer, designated by the thickness variable "A", depends upon the local velocity profile. The local velocity profile is in turn determined by such variables as the volume of fluid delivered through the pathway in a given time period, the cross-sectional area of the fluid pathway, particularly at the tablet, and the configuration of the fluid pathway cross-section. The left set of arrows in FIG. 10 schematically illustrate the local velocity profile at a relatively low flow rate while the right set of arrows in FIG. 10 illustrate the local velocity profile at a relatively high fluid flow rate, wherein the length of the arrows are proportional to the velocity of the fluid at that point in the fluid pathway cross-section.

Conforming with known principles of fluid dynamics, the fluid velocity is greater at the central portion of the fluid pathway and lower at the pathway walls such as defined for example by the housing wall 197 and the tablet surface 204. At lower flow rates, the change in fluid velocity at different points across the fluid pathway cross-section is less than at higher flow rates as indicated by the left and right sets of arrows respectively. By carefully matching the above-discussed tablet characteristics and the configuration of the fluid pathway in the apparatus 168 or the apparatus 60, below a certain fluid flow rate transition region the mass transfer resistance of the diffusional boundary layer is significant, i.e., the value of "A" is high in relation to the mass transfer resistance characteristic of the tablet 182, 200. At fluid flow rates above the transition region, the increased fluid velocity and the resulting greater change in the local velocity profile decrease the thickness "A" of the diffusional boundary layer enough that essentially all of the mass transfer resistance results from the mass transfer resistance in the tablet 182, 200, not from the mass transfer resistance of the diffusional boundary layer. When this occurs the delivery rate of the beneficial agent becomes independent of the fluid flow rate.

Even more important is the ability to match the tablet and the above-described variables associated therewith to the fluid pathway in the apparatus 60, 168 to control the fluid flow rate range of the flow rate transition region. Stated differently, by changing the carrier, the beneficial agent, the fluid pathway and the interrelated characteristics as described above, it is not only possible to create a range of flow rate dependent agent delivery (second mode); the fluid flow rate region values where the agent delivery shifts from dependence upon to independence from fluid flow rate can also be controlled.

This ability to control the fluid flow rate transition region and to make the fluid flow rate transition region high enough to prevent local toxicity at low fluid flow rates in the apparatus 60,168 is a major distinction from other passive reconstitution systems.

At a given flow rate, two different apparatus 60, 168 can have two different local velocity profiles. Thus, the flow rates determining the flow rate transition region can be changed by varying the tablet, which may or may not have a carrier therein, in order to change its mass transfer resistance, or by changing the configuration of the fluid pathway in the housing 78, 170 and particularly the configuration of the chamber 106, 171 to change the local velocity profile and thus the thickness of the diffusional boundary layer.

The inherent rate of dissolution of the beneficial agent to be delivered and the carrier if any used therewith, and the resulting form, e.g., tablet, pellet or powder, in which the beneficial agent is placed within the apparatus, will also determine the configuration and cross-sectional area of the fluid pathway in the apparatus across the surface area of the beneficial agent. The importance of the interaction of the mass transfer resistance provided by a diffusional boundary layer with the mass transfer resistance of the beneficial agent/carrier is illustrated by the horizontal line plotted in FIG. 5 just below the 17 minute mark. The line was plotted by using a tablet such as described above. The tablet was placed in a large vessel containing a liter of water which was stirred virgorously. Such an arrangement effectively eliminates any diffusional boundary layer around the beneficial agent. The horizontal line in the graph of FIG. 5 represents the intrinsic delivery rate of agent from the tablet as determined by the experiment in the large vessel. This intrinsic delivery rate is the rate approached by the first delivery mode in the example.

Figure 11:
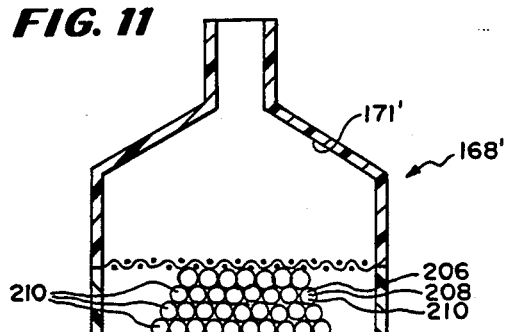
FIG. 11 is a cross-sectional view of a housing with pellets therein.

It is important to note that the apparatus 60, 168 need not have the beneficial agent or combination beneficial agent/carrier in tablet form only. Referring to FIG. 11, there is seen an apparatus 168' similar to the apparatus 168 of FIG. 6, except that it contains a beneficial agent 206 and a carrier 208 in pellet form. Each of the pellets 210 may be made like the individual tablet 182. For example, each pellet 210 may include sodium ampicillin and porous polypropylene. In operation, the apparatus 168' functions like the apparatus 168, except that the flow patterns 168 across and around the pellets 210 are more complex than the flow patterns around the tablet 182.

Figure 12:
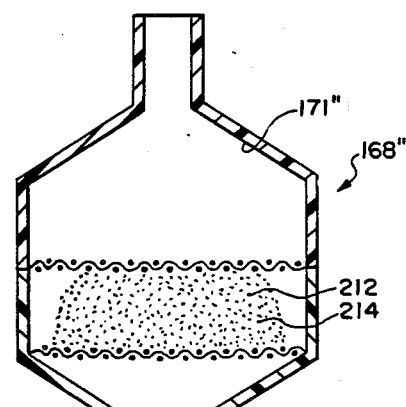
FIG. 12 is a cross-sectional view of a housing having powder therein.

Referring to FIG. 12 there is illustrated an apparatus 168" similar to the apparatus 168, 168', except that the chamber 171" includes very small particles or powder of a beneficial agent 212 and a carrier 214. Continuing with the example, the agent 212 may be sodium ampicillin or another drug and the carrier 214 may be porous polypropylene or a dissolvable sustance. In the apparatus 168" of FIG. 12, the agent 212 particles and carrier 214 particles are provided separately into the chamber 171". However, it would also be possible to combine the agent and carrier into small particles much smaller than the pellets illustrated in FIG. 11. It is believed that this will work better than the separate particles of agent and carrier. The flow patterns in the apparatus 168" may even be more complex than the flow patterns operating in the apparatus 168 of FIG. 11. However, since the agent 212 and carrier 14 are not compressed together in the apparatus 168″, it is believed that the set rate of substantially flow rate independent agent delivery would be higher than in the apparatus 168′, 168.

Furthermore, it is important to note that the pellet form and the powder form represented in FIGS. 11 and 12 may work as well in or even better in an upward directed fluid flowpath such as illustrated in by the apparatus 60 shown in detail in FIGS. 3 and 4.

Figure 13:
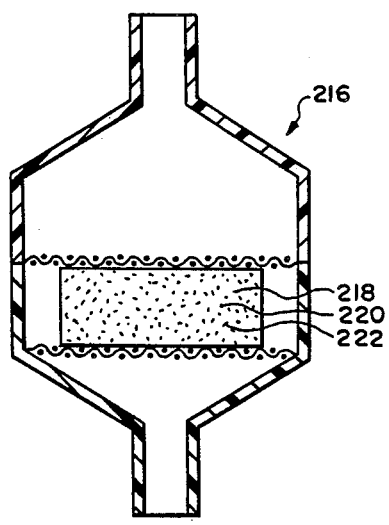
FIG. 13 is a cross-sectional view of a housing having a tablet therein including a beneficial agent and a dissolvable carrier.

Referring now to FIG. 13, there is illustrated an apparatus 216 similar to the apparatus 168. The apparatus 216 includes a tablet 218 comprising a beneficial agent 220 and a dissolvable carrier 222, such as mannitol. The beneficial agent may be sodium ampicillin. In this example, the amount of carrier necessary is much higher than with the nondissolvable carrier. For example the weight ratio of carrier 222 to beneficial agent 220 may be 10:1. The control means operates such as described above, including reliance upon a larger diffusional boundary layer at lower flow rates to create a second delivery mode of flow rate dependent agent delivery. At higher flow rates agent delivery is substantially independent of fluid flow rate. However, since the carrier 222 dissolves along with the agent 220, the maximum rate of agent dissolution is controlled less by the mass transfer resistance created by the tablet 218 and more by the solubility of the carrier 222 competing with the agent 220 for the available fluid. Stated differently, with a dissolvable carrier 222 the intrinsic rate of dissolution of the tablet 218 most likely replaces the mass transfer resistance of the tablet 182 as the critical factor in determining maximum agent delivery rate.

It is believed that the combined beneficial agent 220 and dissolvable carrier 222 may be employed in powder and pellet form as illustrated in FIGS. 11 and 12 for a nondissolvable carrier. In addition, the combination of an agent 220 with a dissolvable carrier 222 may be used in the apparatus 60.

With both a nondissolvable carrier and a dissolvable carrier it is important not only to have a properly sized flowpath across and around the agent, but also important to limit the size of the chamber in which the agent is stored, thereby limiting the amount of dissolved concentrated agent present within the cartridge.

It is believed that with either a dissolvable or nondissolvable carrier, the powder form illustrated in FIG. 12 is more sensitive than either the pellet or tablet form to increased flow rates, because the greater turbulence caused by greater flow rate will have a greater effect upon increasing the rate of agent dissolution in the powder form. Also, it is believed that with the powder form the fluid flow rate transition region may be harder to control.

It is believed that a dissolvable carrier 222 may create a system which is more influenced by an increased flow rate than an insoluble carrier; however, use of a dissolvable carrier does ensure a substantially constant agent delivery rate over time at higher flow rates.

One advantage of a dissolvable carrier 222 is that it provides a visual indicator of whether or not the dose of beneficial agent 222 has been delivered out of the apparatus 60, 168. For example, the tablet 218, having a dissolvable carrier may be placed in the cartridge 82 of the apparatus 60. The cartridge 82 may be optically transparent to enable viewing of the chamber 106. A nurse or other operator could tell that the agent 220 had been substantially delivered by noting that the tablet 218 had dissolved. Such an arrangement may eliminate the need for the hollow plastic sphere 129 or other floating indicator.

Referring now to FIG. 14, there is schematically illustrated a split fluid pathway having two non-series connecting fluid pathway segments **224*a*, 224*b* in a fluid pathway of an apparatus 226. The schematically illustrated apparatus 226 includes a beneficial agent 228 in loose powder form for example, trapped between screen mesh 230 for example. FIG. 14 illustrates the use of a split flow path to help create a second delivery mode high enough to prevent local agent toxicity in the fluid delivered to a patient. By properly sizing the non-series connecting segments 224*a*, 224*b*, the apparatus 226 may be designed so that at a flow rate of 60 ml/hour for example, 20 ml/hour goes through segment 224*a* and 40 ml/hour flows through segment 224*b*. Because of resistance caused by the beneficial agent 228 in the segment 224*a*, the segment 224*b*** may have a much smaller cross-sectional area.

With this construction, raising the fluid flow rate from 60 to 120 ml/hour would result in approximately 40 ml/hour through the segment **224*a* and 80 ml/hour through the segment 224*b*. Similarly, lowering the fluid flow rate to 30 ml/hour would result in approximately 10 ml/hour through the segment 224*a* and 20 ml/hour through the segment 224 *b*. Depending on the inherent rate of dissolution of the beneficial agent 228, the delivery of agent 228 out the outlet 232 at flow rates of 60 and 120 ml/hour may be independent of fluid flow rate, whereas at the lower flow rate of 30 ml/hour, the flow of liquid through the segment 224*b*** may become determinative of the agent delivery rate, so that agent delivery becomes dependent upon the fluid flow rate.

It will be seen that with the split-flow arrangement of the apparatus 226, the restriction of fluid flow across the segment **224*a* may vary greatly over time, as the beneficial agent 228 dissolves. The effect of this change may be decreased by employing a nondissolvable carrier or it may be hard to develop such a construction without blocking flow through the segment 224*a* entirely. Thus, it may be seen that the apparatus 226 is better directed to the delivery of a beneficial agent 228 over much longer time periods such as for example twenty-four hours. By so doing, the change in fluid flow resistance through the segment 224*a*** will be less per unit time, allowing for a more substantially flow rate independent agent delivery at flow rates at or above a certain desired value.

FIG. 15 illustrates an apparatus 234 which is similar in appearance to the apparatus 60 shown in FIGS. 3 and 4, but which functions quite differently. The apparatus 234 employs the split-flow fluid pathway as discussed with reference to the apparatus 226. When the cartridge 82' is plugged into the receptacle 80' without a flow director, some fluid continues to flow out the outlet 96', without first flowing through the cartridge 82' with a beneficial agent 236 therein. The apparatus 234 is not preferred, especially for smaller agent delivery time periods such as about thirty minutes.

It is important to note that the agent or agent/carrier combination placed in the chamber of the apparatus 60, 168, 168' , 168", 216, 226, 234 may include other configurations and, when correctly matched with the proper flowpath for creation of a specific local velocity profile and diffusional boundary layer, comprise control means creating a second delivery mode which extends to fluid flow rates high enough to prevent local agent toxicity. For example, the agent and carrier may comprise drug particles essentially completely coated by polymer. Another possibility is drug contained in an internal tablet-sized mass transfer conductor or reservoir, said conductor or reservoir surrounded by an outer, rate controlling membrane. Fluid flow would be directed over the membrane. Further possibilities include bio-erodible or water-erodible carriers containing agent particles wherein the products of the erosion inhibit further net erosion, and agent particles with a non-dissolvable carrier wherein a tortuous agent release pathway is created. Still further possibilities of carrier types and carrier/agent combinations are illustrated in U.S. Pat. Nos. 4,424,056; 4,432,756; and 4,439,183 for example. Referring now to FIGS. 16 and 17, there is illustrated an apparatus 238 for placement in an intravenous delivery system such as shown in FIG. 1, replacing the apparatus 60. A fluid conduit such as plastic tubing 76' includes upstream tubing portion 76a' adapted for connection to a fluid source and downstream tubing portion 76b' adapted for fluid communication with a patient's intravenous system.

The apparatus 238 includes a housing 240 having a receptacle 242 including an inlet 244 connected to the upstream portion 76a' of the fluid conduit and an outlet 246 connected to the downstream portion 76b' of the fluid conduit. The receptacle 242 may be an injection site of virtually standard construction, such as the "Y" adapter injection site 36 shown in the prior art system of FIG. 2.

The housing 240 includes a separate cartridge 248 which is plugged into the receptacle 242 to form the complete housing 240. The housing 240 may also be constructed so that the cartridge 248 and the receptacle 242 are a unit.

Like the housing 78, the housing 240 defines a fluid pathway 250 therethrough. The inlet 244 and the outlet 246 define part of the fluid pathway 250. The fluid pathway forms part of the fluid conduit of the intravenous delivery system.

The housing includes a fluid receiving segment 252 having an upstream end 254 in fluid communication with the inlet 244, and a downstream end 256. A chamber 258 adapted for receiving a beneficial agent 260 and a carrier 262, such as pellets 264 of sodium ampicillin and porous polypropylene for example, is defined by the cartridge 248. The chamber 258 defines part of the fluid pathway 250 in the housing 240.

The receptacle 242 preferably includes a handle 243 for grasping the receptacle 242 when attaching the cartridge 248. The receptacle 242 includes a polyisoprene or other puncturable, resealable situs 266 closing off an access volume 268 defined by the wall 270 of the receptacle 242. The wall 270 also defines a narrower channel 272 adjacent the outlet 246.

The cartridge 248 includes a double bore needle 274 adapted for piercing the receptacle situs 266. The double bore needle 274 is mounted to the cartridge wall 276 so that both bores of the needle 274 are in communication with the chamber 258. A cartridge sleeve 278 mounted about and spaced from the double bore needle 274 prevents touch contamination of the needle 274 and assures a secure fit of the cartridge 248 to the receptacle 242. A slot 280 in the sleeve 278 fits around the fluid receiving segment 252 of the receptacle 242. A tip protector 282 closes the sleeve 278 and double bore needle 274 during storage and is removed before attaching the cartridge to the receptacle.

The cartridge 248 further includes a holding loop 284 for securing the cartridge to the upstream tubing portion 76a'.

The chamber 258 includes a chamber upstream end 286 adapted for fluid communication with the receiving segment downstream end 256, and a chamber downstream end 294, opposite the upstream end 286.

The first and second bores 290, 298 of the double bore needle 274, along with the situs 266, form connecting means for securing the cartridge 248 to the receptacle 242 and providing for fluid flow therebetween. The connecting means includes first and second cross-over segments which correspond to the first and second bores 290, 298. The first cross-over segment, in this case the first bore 290, is disposed between and adapted for providing fluid communication between the receiving segment downstream end 256 and the chamber upstream end 286.

In the housing 240 the second cross-over segment, in this case the second bore 298, comprises the discharge segment 296, so that the second cross-over segment is disposed between and adapted for fluid communication between the chamber downstream end 294 and the outlet 246. The discharge segment 296 includes a discharge segment upstream end 300 which is the open end of the second bore 298 within the chamber 258, adapted for fluid communication with the chamber downstream end 294. The discharge segment downstream end 302 is defined by the open distal end 304 of the second bore 298.

The access volume 268, as closed by the situs 266, also forms part of both the first and second cross-over segments. Thus, the first and second cross-over segments are each disposed in both the receptacle 242 and the cartridge 248.

The situs 266 comprises puncturable means. The closed distal end 288 of the first bore 290 and the open distal end 304 of the second bore 298, all being part of the double bore needle 274, comprise the puncturing means.

When the cartridge 248 is not plugged into the receptacle 242, fluid flowing from the fluid source through the fluid conduit 76' flows through the housing inlet 244 and into the receiving segment 252. The fluid flows out the receiving segment downstream end 256, whereupon it continues to flow out the outlet 246 into the downstream portion 76b' of the tubing 76'.

When the cartridge 248 is plugged into the receptacle 242 such that the chamber 258 is in fluid communication with the receiving segment 252 and the discharge segment 296, the double bore needle 274 seals against the narrower channel 272 within the receptacle 242 so that fluid entering the receiving segment 252 does not exit immediately into the outlet 246 but must instead first enter the double bore needle 274. Fluid flows from the receiving segment downstream end 256 into the first side opening 292 of the first bore 290 and up the first bore 290. Fluid exits the first bore 290 at the second side opening 293 of the first bore 290, into the chamber 258 at the chamber upstream end 286. The fluid flows up through and around the beneficial agent 260 and carrier 262 upwardly to adjacent the chamber upstream end 294, whereupon it begins to flow downwardly through the discharge segment 296 and then through the outlet 246.

The beneficial agent 260 may be combined with a carrier 262 and may be in powder, pellet, tablet or other form. The carrier may be dissolvable or non-dissolvable. When the limits of agent dissolution provided by the tablet, pellet, powder or other agent or agent/carrier configuration are combined with the limitations of the flowpath in the housing 240, the apparatus 238 thereby includes control means necessary to push the fluid flow rate transition region up into a flow rate range permitting flow rate dependent agent delivery at flow rates high enough to prevent local toxicity.

Even without the control means the housing 240 permits passive drug reconstitution and includes all the advantages provided by an upward flowpath as discussed with reference to the housing 78. Similar to the housing 78, the housing 240 allows for delivery of the beneficial agent 260 in a time period short enough to be therapeutically effective. However, the housing 240 prevents the drug from being delivered too quickly at high flow rates so that the medically unacceptable condition of systemic toxicity will not occur.

As with the housing 78, it is believed that air eliminating means should be included in the fluid conduit of the intravenous delivery system including the housing 240. However, as with the housing 78, the air eliminating means need not be disposed within the housing 240 itself, but rather may be disposed downstream of the housing.

As with the housing 78, the housing 240 may be designed for shipment to a hospital with the beneficial agent therein, or designed for agent filling at the hospital.

The slot 280 in the cartridge sleeve 278 along with the sleeve 278 itself provides a key way to assure that the first side opening 292 is disposed facing the upstream tubing portion 76', although it is believed that even if the first side opening 292 were rotated 180° the housing 240 would still function properly.

Figure 19:
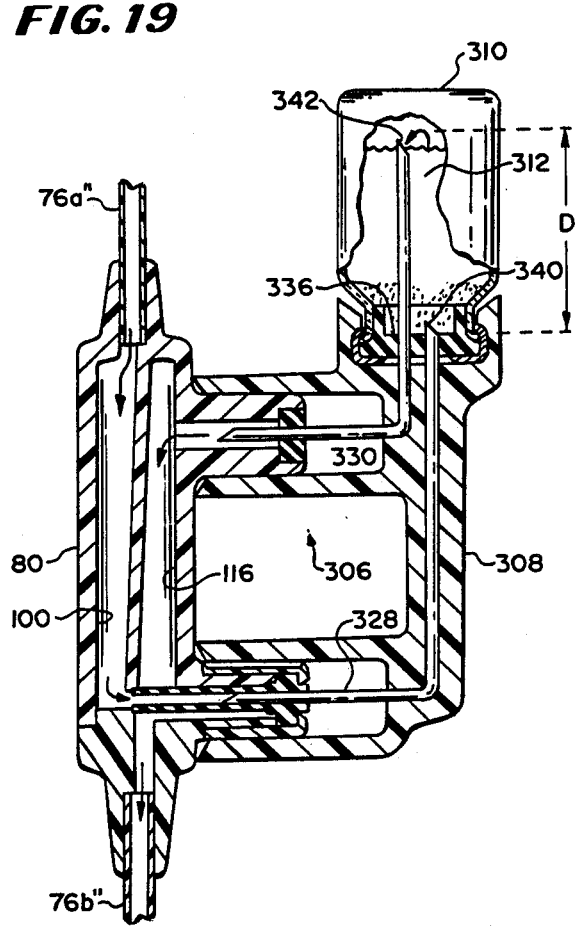
FIG. 19 is a cross-sectional view of the housing illustrated in FIG. 18, but with the intermediate portion of the receptacle secured to both the "in-line" portion of the receptacle and the cartridge.

Referring now to FIGS. 18 and 19 there is disclosed yet another housing 306, including a receptacle 80 which may be identical to the receptacle in the housing 78. The receptacle 80 is mounted "in-line" in an intravenous delivery system between upstream and downstream portions 76a", 76b" respectively of plastic tubing 76".

The housing 306 includes a separate receptacle 80, intermediate portion 308 and cartridge 310. The cartridge 310 may be a drug vial of standard construction. The ability to use a drug vial of standard construction represents one of the advantages of the housing 306. FIG. 18 illustrates the three separate units. Before the three units are connected, fluid flows through the receiving segment 100 from the inlet 94 to the outlet 96. FIG. 19 illustrates the housing 306 with the three units 80, 308, 310 connected so that virtually all fluid which flows out of the outlet 96 first flows through all three of the receiving segment 100, the chamber 312 defined by the cartridge 310, and the discharge segment 116, forming a fluid pathway in the housing 306.

When the cartridge 310 is a drug vial of standard construction, it typically includes an optically transparent glass wall 314 defining the chamber 312 and a container neck 316. A stopper 318 or situs of rubber or other puncturable, resealable material is mounted within the mouth 320 defined by the neck 316. A metal band 322 is secured about the mouth 320, retaining the stopper 318 in the cartridge 310.

Connecting means allow for fluid communication between the receptacle 80, the intermediate portion 308 and the cartridge 310. The connecting means includes first and second cross-over segment 324, 326. Portions of both the first and second cross-over segments are included in the receptacle 80. Injection sites 126, 128 block the first and second cross-over segments 324, 326 in the receptacle 80 and serve as the puncturable means as described above with reference to the housing 78. Puncturing means for the injection sites 126, 128 include first and second intermediate cannulas 328, 330 mounted within the intermediate portion 308 and serving as part of the first and second cross-over segments 324, 326 respectively. The intermediate portion 308 includes sleeves 332, 334 mounted about and spaced from the portions of the cannulas 328, 330 respectively which pierce the injection sites 126, 128, preventing touch contamination.

When disposed as shown in FIG. 19, the chamber upstream end 336 is adjacent the rubber stopper 318 and the chamber downstream end 338 is the end opposite the stopper. The first and second cross-over segments 324, 326 include sharpened vial ends 340, 342 for puncturing the stopper 318. The first cross-over segment vial end 340 is sized so as to just pierce the stopper 318, projecting just slightly into the chamber 312. The second cross-over segment vial end 342 projects much further into the chamber 312, closer to the chamber downstream end 338.

The cartridge 310 includes a beneficial agent 344 which is most commonly in a powder form and, as shown in FIG. 19, is disposed within the cartridge neck 316 which has a natural funnel-like configuration.

By placing the first cross-over segment vial end 340 barely within the chamber, a turbulent flow pattern is created around the beneficial agent 344. By placing the second cross-over segment vial end 342 well within the chamber 312, vertically spaced from the first segment vial end 340, an upward flow pattern is created within the chamber 312.

The first cross-over segment 324 provides fluid flow communication between the receiving segment downstream end 104 and the chamber upstream end 336. The second cross-over segment 326 provides for fluid communication between the chamber downstream end 338 and the discharge segment upstream end 118.

The distance between the second segment vial end 342 and the chamber upstream end 336, noted as distance "D", along with the volume of the chamber 312 are two factors which determine the concentration of agent in fluid flowing into the second cross-over segment vial end 342, downstream to the outlet 96. It should be noted that the critical distance "D" also corresponds to the distance between the second side opening 293 and the discharge segment upstream end 300 in the housing 240 of FIGS. 16 and 17.

Raising the first segment vial end 340 will lessen turbulence through the beneficial agent 344 stored in the chamber, lessening the mixing action and thereby relying more on the inherent dissolution rate of the beneficial agent 344 for mixing the agent 344 with the fluid. In addition, the solubility of the beneficial agent and the dose of agent 344 within the chamber may also determine the appropriate distance between the second segment vial end 342 and the stopper 318 (distance "D"), in order to deliver the agent dose within a therapeutically acceptable time period. Listed below are agent, dosage and approximate needle distance "D" and vial (cartridge) volume for each of four drugs tested with a similar housing 306, for delivery of the agent within the prescribed time periods.

| Drug | Dose | Distance "D" | Vial Volume |
|---|---|---|---|
| Ampicillin | 1 gm | 2" | 10 cc |
| Ampicillin | 2 gm | 2" | 20 cc |
| Cephalothin | 1 gm | 1" | 10 cc |
| Cephalothin | 2 gm | 1½" | 20 cc |
| Cefazolin | 0.5 gm | 1½" | 10 cc |
| Cefazolin | 1 gm | 1½" | 10 cc |
| Cefazolin | 2 gm | 1½" | 20 cc |
| Ticarcillin | 1 gm | 1" | 20 cc |
| Ticarcillin | 2 gm | 1½" | 20 cc |
| Ticarcillin | 3 gm | 2" | 30 cc |

The above data are intended to be examples only and may vary. Different needle lengths in the same vial volume for the same dosage weights of different drugs are necessitated because of different drug solubilities and rates of dissolution.

The housing 306 may also be constructed in a manner such as would be represented by turning the intermediate portion 308 and the cartridge 310 upside down with respect to the receptacle 80, so that the second cannula 330 is upstream of the first cannula 328. Furthermore, while the housing 306 is intended for use with a standard drug vial as the cartridge 310, which vials typically have powdered drug therein, the cartridge 310 can instead store a tablet, pellets, powder or other configuration of beneficial agent and carrier as discussed above.

Furthermore, it may be possible, by controlling the variables of chamber volume, cross-sectional configuration of the flow path and locations of the cross-over segment vial ends 340, 342 to create an apparatus which includes the necessary control means to create both first and second delivery modes where the second delivery mode of flow rate dependent agent delivery is at flow rates medically acceptably high enough to prevent local toxicity of agent.

As with the housing 78, the intravenous delivery system including the housing 306 should also include air eliminating means, preferably downstream of the housing 306.

The housing 306 permits passive agent reconstitution and permits the use of standard drug vials used by many companies to contain drugs.

While several embodiments and features have been described in detail herein and shown in the accompanying drawings, it will be evident that various further modifications are possible without departing from the scope of the invention.

What is claimed is:

1. A housing means adapted for insertion in an intravenous delivery system including a fluid source and a fluid conduit, wherein fluid is delivered from the fluid source through the fluid conduit to the intravenous system of a patient, the housing means being adapted for receiving a beneficial agent to be mixed with fluid flowing through the fluid conduit, said housing means comprising:
   (a) a receptacle adapted for insertion into the fluid conduit and including inlet means adapted for connection to an upstream portion of the fluid conduit and outlet means adapted for connection to a downstream portion of the fluid conduit;
   (b) a separate cartridge including a chamber, selectively secured to said receptacle, said chamber adapted for receiving the beneficial agent, said chamber including an upstream end adapted for fluid communication with said inlet means, said chamber further including a downstream end;
   (c) a discharge segment disposed in both said cartridge and said receptacle when said cartridge is secured to said receptacle, including a discharge segment upstream and adapted for communication with said chamber downstream end, and a discharge segment downstream end in communication with said outlet means;
   (d) connecting means in both said receptacle and said cartridge for securing said cartridge to said receptacle;
   (e) whereby when said cartridge is not secured to said receptacle, liquid from the fluid source may still be delivered to the patient through the fluid conduit, including said receptacle, with no liquid leaving said receptacle between said receptacle inlet means and said receptacle outlet means;
   (f) whereby, when said chamber is in fluid communication with said receptacle and said discharge segment, virtually all liquid which flows out said outlet means flows through all three of said inlet means, said chamber and said discharge segment, forming a fluid pathway in said housing; and
   (g) further whereby said chamber downstream end is disposed at an elevation higher than said chamber upstream end, so that the direction of liquid flow through at least a portion of said chamber is in a generally upward direction, generally opposite to the direction of liquid flow from the fluid source to the patient;
   (h) such that as fluid flows through said housing, the beneficial agent in said chamber mixes with the liquid and is delivered therewith to the patient.

2. The housing in accordance with claim 1, wherein said receptacle also comprises said discharge segment.

3. The housing in accordance with claim 1, wherein said cartridge includes a wall defining said chamber and a mouth to said chamber, and further comprising a pierceable stopper disposed in and sealing said mouth, said cartridge being adapted to plug into the remainder of said housing so that said chamber is in fluid communication with both said inlet means and said discharge segment through said single stopper.

4. The housing in accordance with claim 1, further comprising: (a) first cross-over segment disposed between and adapted for providing fluid communication between said inlet means and said chamber upstream end; and (b) a second cross-over segment disposed between and adapted for fluid communication between said chamber downstream and said outlet means.

5. The housing in accordance with claim 4, wherein said second cross-over segment is disposed between and adapted for fluid communication between said chamber downstream end and said discharge segment upstream end.

6. The housing in accordance with claim 4, wherein said first cross-over segment includes a first segment end and wherein said second cross-over segment includes a second segment end, said ends being disposed within said chamber.

7. The housing in accordance with claim 6, wherein said second segment end and first segment end are disposed at different elevations within said chamber, said second segment end being downstream of said first segment end and said second segment end being closer to said chamber downstream end than said first segment end.

8. The housing in accordance with claim 4, wherein said first cross-over segment comprises a flow director disposed in said receptacle, said receptacle having a receiving segment immediately downstream of said inlet means, said flow director including:
(a) a tube having a upstream end fluid-sealingly connected to said receiving segment downstream end, and an opposite end;
(b) a puncturable, resealable injection site occluding said first cross-over segment, connected to said opposite end of said tube; and
(c) a flow-bypass opening defined in said tube, such that when said cartridge is not secured to said receptacle, fluid flowing into said receptacle flows into said flow director, and out of said flow director at said flow-bypass opening, to said outlet.

9. The housing in accordance with claim 4, wherein said connecting means comprises said first and second cross-over segments.

10. The housing in accordance with claim 9, further comprising:
(a) puncturable means disposed in and blocking both said first and second cross-over segments; and
(b) puncturing means in both said first and second cross-over segments for puncturing said puncturable means, such that when said cartridge and said receptacle are urged together, said puncturing means pierces said puncturable means, placing said inlet means and said discharge segment in fluid communication.

11. The housing in accordance with claim 10, wherein said puncturable means comprise resilient, rubber-like injection sites.

12. The housing in accordance with claim 11, wherein said puncturing means comprise pointed cannulas, said cannulas forming part of said first and second cross-over segments.

13. The housing in accordance with claim 10, wherein said first cross-over segment comprises a flow director disposed in said receptacle, said receptacle having a receiving segment immediately downstream of said inlet means and which includes:
(a) a tube having an upstream and fluid-sealingly connected to said receiving segment downstream end, and an opposite end;
(b) a puncturable, resealable injection site including said first cross-over segment puncturable means, connected to said opposite end of said tube; and
(c) a flow-bypass opening defined in said tube, such that when said cartridge is not secured to said receptacle, fluid flowing into said receptacle flows into said flow director, and out said flow director at said flow-bypass opening, to said outlet.

14. The housing in accordance with claim 13, wherein said puncturing means comprises a pointed cannula, such that when said cartridge is secured to said receptacle, said cannula pierces said flow director injection site and fluid flowing into said receptacle flows into said flow director tube, virtually all of said fluid in said flow director tube flowing into said cannula, downstream to said outlet.

15. The housing in accordance with claim 14, in which said flow director tube is resilient and sized so as to seal about the outer periphery of said hollow cannula, prevention fluid flowing into said flow director tube from flowing out said flow-bypass opening when said cartridge is secured to said receptacle.

16. The housing in accordance with claim 14, wherein said flow director intercepts but does not occlude said discharge segment.

17. The housing in accordance with claim 1, wherein said chamber upstream portion includes a funnel-like configuration, widening in the downstream direction.

18. The housing in accordance with claim 1, wherein said chamber downstream portion includes a funnel-like configuration, narrowing in the downstream direction.

19. The housing in accordance with claim 1, further comprising air eliminating means in the fluid conduit for eliminating air entrained in the fluid conduit, said air eliminating mean being disposed in a position which is one of (a) in said chamber and (b) downstream of said chamber.

20. The housing in accordance with claim 1, wherein said cartridge, when secured to said receptacle, is devoid of any means for directing air entrained in the fluid conduit out of said cartridge into the environment external of the intravenous delivery system, without the entrained air first flowing downstream of said cartridge.

21. The housing in accordance with claims 1, further comprising a portion of the chamber wall being optically transparent, said chamber including a floating visual indicator therein, other than the beneficial agent, that, because of changing specific gravity of the fluid, changes elevation upon completion of mixing of the beneficial agent and delivery of the agent downstream of said chamber.

22. The housing in accordance with claims 1, further comprising a portion of the chamber wall being optically transparent, and including a plurality of floating visual indicators, other than the beneficial agent, in said chamber, said indicators being able to float in fluids of different specific gravity ranges, such that as mixing nears completion, certain of said visual indicators begin to drop and such that after mixing is complete and after the beneficial agent has been delivered out said chamber, all of said visual indicators have dropped.

23. The housing in accordance with claims 1 further comprising portions of the housing defining said receptacle and said cartridge being optically transparent, each including a plurality of floating visual indicators therein, other than the beneficial agent, said floating visual indicators within said, receptacle being able to float in fluids of different specific gravity ranges, and said visual indicators within said cartridge being able to float in fluids of different specific gravity ranges, but the same ranges as said indicators in said receptacle, wherein visual confirmation of complete mixing and delivery of the agent downstream of said chamber is made when the same number of visual indicators remain floating in said chamber as in said receptacle.

24. The housing in accordance with claim 1, further comprising a portion of the housing defining said discharge segment being optically transparent, said discharge segment including a floating visual indicator therein, other than the beneficial agent, that, because of changing specific gravity in the fluid, changes elevation upon completion of mixing of the beneficial agent and delivery of the agent downstream of said discharge segment.

25. The housing in accordance with claim 1, further comprising a portion of the discharge segment wall being optically transparent, and including a plurality of floating visual indicators, other than the beneficial agent, in said discharge segment, said indicators being able to float within fluids of different specific gravity ranges, such that as mixing nears completion, certain of said visual indicators begin to drop and such that after mixing is complete and after the beneficial agent has been delivered out said discharge segment, all of said visual indicators have dropped.

26. The housing in accordance with claim 1, further comprising portions of the housing defining said receptacle and said discharge segment being optically transparent, each of said discharge segment and said receptacle including a plurality of floating visual indicators therein, other than the beneficial agent, said floating visual indicators within said receptacle being able to float in fluids of different specific gravity ranges, and said visual indicators within said discharge segment being able to float in fluids of different specific gravity ranges, but the same ranges as said indicators in said receptacle, wherein visual confirmation of complete mixing and delivery of the agent downstream of said discharge segment is made when the same number of visual indicators remain floating in said discharge segment as in said receptacle.

27. The housing in claim 1, further wherein said connecting means includes means for disengagement of said cartridge from said receptacle, to permit another of said cartridges to be sequentially operatively secured to, and disengaged from, said receptacle.

28. The housing as in claim 1, wherein said connecting means includes said discharge segment.

29. The housing as in claim 1, wherein said receptacle further comprises narrower channel means cooperating with said discharge segment to ensure that all liquid flowing out said outlet mean flows through said chamber.

30. The housing as in claim 1, wherein said cartridge also comprises said discharge segment.

31. The housing as in claim 4, wherein said second cross-over segment comprises said discharging segment.

32. The housing means as in claim 1 further comprising a first cross-over segment means for placing said inlet means in fluid communication with said chamber upstream end.

33. The housing means as in claim 1, further comprising a second cross-over segment means for placing said chamber downstream end in fluid communication with said outlet means.

34. The housing means as in claim 1, said receptacle further comprising narrower channel means forming part of the fluid pathway through the receptacle, said narrower channel means being disposed along said receptacle fluid pathway, at a location between said inlet means and said outlet means, said narrower channel means cooperating with said discharge segment such that when said cartridge is operatively secured to said receptacle, said narrower channel means seals against said discharge segment, so that virtually all liquid that flows out said outlet means flows through said receptacle inlet means, said cartridge and said discharge segment.

35. A method for mixing a beneficial agent with fluid flowing from a fluid source through a fluid conduit to a patient, the steps comprising:
 (a) providing a receptacle having fluid inlet means and outlet means in the fluid conduit, adapted for having a separate cartridge selectively, operatively secured thereto and permitting, when the cartridge is not secured to the receptacle, liquid from the fluid source to be delivered to the patient through the fluid conduit including the receptacle, with no liquid exiting the receptacle between the inlet means and outlet means;
 (b) providing a separate cartridge defining a chamber carrying a beneficial agent therein, the chamber including an upstream end adapted for fluid communication with the receptacle inlet means when the cartridge is operatively secured to the receptacle, the chamber further including a downstream end;
 (c) providing a discharge segment disposed in both the cartridge and the receptacle when the cartridge is operatively secured to the receptacle, the discharge segment further including an upstream end adapted for communication with the chamber downstream end and a discharge segment downstream end in communication with the outlet means when the cartridge is operatively secured to the receptacle; and
 (d) operatively securing the cartridge to the receptacle, thereby:
  (i) directing virtually all liquid through the receptacle inlet means, the chamber and the discharge segment before flowing out of the receptacle outlet means; and
  (ii) disposing the chamber downstream end at an elevation higher than the chamber upstream end, thereby;
  (iii) directing fluid flow through at least a portion of the chamber in a generally upward direction, generally opposite to the direction of fluid flow from the fluid source to the patient;
  (iv) such that as liquid flows through the cartridge, the beneficial agent in the chamber mixes with the liquid and is delivered therewith to the patient.

36. The method of claim 35, further comprising removing the cartridge from the receptacle to subsequently permit liquid flow through the receptacle to the patient.

37. The method of claim 36, further comprising operatively securing another cartridge to the receptacle.

38. The method as in claim 35, further comprising the step of providing the beneficial agent in the cartridge in powder form.

39. A receptacle adapted for insertion in an intravenous delivery system including a fluid source and a fluid conduit, wherein fluid is delivered from the fluid source through the fluid conduit to the intravenous system of a patient, said receptacle comprising:
 (a) an inlet adapted for connection to an upstream portion of the fluid conduit;
 (b) a fluid receiving segment having an upstream end in fluid communication with said inlet, and a downstream end;
 (c) an outlet adapted for connection to a downstream portion of the fluid conduit.
 (d) a discharge segment including an upstream end in fluid communication with an injection site adapted for communicating with the downstream end of a separate cartridge, and a discharge segment downstream end in communicating with said outlet; and
 (e) a flow director, said flow director including:
  (i) a tube having an upstream end fluid-sealingly connected to said receiving segment downstream end, and an opposite end (ii) a puncturable, resealable injection site secured to said opposite end for communicating with the upstream end of a separate cartridge, and (iii) a flow-bypass opening defining in said tube;

(f) such that when the separate cartridge is not connected to said receptacle, fluid entering said receptacle at said inlet flows sequentially through said receiving segment, said flow director tube, said flow director bypass opening and said outlet, wherein said flow director intercepts but does not occlude said discharge segment;

(g) wherein said flow director tube is resilient and effectively seals around the outer periphery of a cartridge cannula inserted through said flow director injection site, such that when the separate cartridge is secured to said receptacle, fluid entering said receptacle at said inlet flows sequentially through said receiving segment, said flow director tube, the cartridge cannula, the cartridge, said discharge segment and said outlet, said receptacle being thereby virtually devoid of fluid flow through said flow director flow-bypass opening.

40. A cartridge for selective securement to an associated receptacle, for introducing a beneficial agent into an intravenous delivery system including a fluid source, a fluid conduit and the receptacle in the conduit, the receptacle including inlet means communicating with an upstream portion of the fluid conduit and outlet means communicating with a downstream portion of the fluid conduit, such that when said cartridge is not secured to the receptacle, liquid from the fluid source may still be delivered through the fluid conduit through the receptacle, said cartridge comprising:

(a) a wall defining a chamber adapted for receiving a beneficial agent to be delivered through the intravenous delivery system, at least a portion of said chamber wall being optically transparent;

(b) said defined chamber including
  (i) an upstream end adapted for fluid communicating with the receptacle inlet means when said cartridge is operatively secured to the receptacle and
  (ii) a downstream end;

(c) a discharge segment including
  (i) a discharge segment upstream end for fluid communication with said chamber downstream end and
  (ii) a discharge segment downstream and extending outside said chamber for fluid communication with the receptacle outlet means; and (d) connecting means for selectively, operatively securing said cartridge to the associated receptacle so that said chamber downstream end is disposed at an elevation higher than said chamber upstream end, said connecting means also thereby disposed for directing fluid flow through at least a portion of said chamber in a generally upward direction;

(e) whereby, when said cartridge is operatively secured to the associated receptacle by said connecting means, virtually all fluid which flows out of and downstream of the receptacle outlet means flows through said chamber-defining cartridge and said discharge segment, forming a fluid pathway through said cartridge;

(f) such that as liquid flows through said defined chamber, the beneficial agent in said chamber mixes with the liquid and is delivered therewith to the patient;

(g) said defined chamber further including a floating visual indicator therein other than the beneficial agent, that, because of changing specific gravity of the fluid, changes elevation upon completion of mixing of the beneficial agent and delivery of the agent downstream of said chamber.

41. A cartridge for selective securement to an associated receptacle, for introducing a beneficial agent into an intravenous delivery system including a fluid source, a fluid conduit and the receptacle in the conduit, the receptacle including inlet means communicating with an upstream portion of the fluid conduit and outlet means communicating with a downstream portion of the fluid conduit, such that when said cartridge is not secured to the receptacle, liquid from the fluid source may still be delivered through the fluid conduit through the receptacle, said cartridge comprising:

(a) a wall defining a chamber adapted for receiving a beneficial agent to be delivered through the intravenous delivery system, at least a portion of said chamber wall being optically transparent;

(b) said defined chamber including
  (i) an upstream end adapted for fluid communication with the receptacle inlet means when said cartridge is operatively secured to the receptacle and
  (ii) a downstream end;

(c) a discharge segment including
  (i) a discharge segment upstream end for fluid communication with said chamber downstream end and
  (ii) a discharge segment downstream end extending outside said chamber for fluid communication with the receptacle outlet means; and (d) connecting means for selectively, operatively securing said cartridge to the associated receptacle so that said chamber downstream end is disposed at an elevation higher than said chamber upstream end, said connecting means also thereby disposed for directing fluid flow through at least a portion of said chamber in a generally upward direction;

(e) whereby, when said cartridge is operatively secured to the associated receptacle by said connecting means, virtually all fluid which flows out of and downstream of the receptacle outlet means flows through said chamber-defining cartridge and said discharge segment, forming a fluid pathway through said cartridge;

(f) such that as liquid flows through said defined chamber, the beneficial agent in said chamber mixes with the liquid and is delivered therewith to the patient;

(g) said defined chamber further including a plurality of floating visual indicators other than the beneficial agent, said indicators being able to float in fluids of different specific gravity ranges, such that as mixing nears completion, certain of said visual indicators begin to drop and such that after mixing is complete and after the beneficial agent has been delivered out said chamber, all of said visual indicators have dropped.

* * * * *

UNITED STATES PATENT AND TRADEMARK OFFICE
CERTIFICATE OF CORRECTION

PATENT NO. : 4,874,366

DATED : October 17, 1989

INVENTOR(S) : Brian Zdeb, Steve Pearson, Glenn L. Slater

It is certified that error appears in the above-identified patent and that said Letters Patent is hereby corrected as shown below:

In column 26, at line 7, delete "upstream and" and substitute --upstream end-- therefor.

In column 26, at line 53, after "downstream", insert --end--.

In column 27, at line 17, delete "out of said flow" and substitute --out said flow-- therefor.

In column 27, at line 46, delete "upstream and" and substitute --upstream end-- therefor.

In column 27, at line 68, delete "prevention" and substitute --preventing-- therefor.

In column 28, at line 15, delete "mean" and substitute --means-- therefor.

In column 29, at line 24, after "housing", insert --as--.

In column 29, at line 34, delete "mean" and substitute --means-- therefor.

In column 29, at line 39, delete "discharging" and substitute --discharge-- therefor.

In column 30, at line 68, after "opposite end" insert --,--.

In column 31, at lines 40 and 41, delete "communicating" and substitute --communication-- therefor.

UNITED STATES PATENT AND TRADEMARK OFFICE
CERTIFICATE OF CORRECTION

PATENT NO. : 4,874,366

DATED : October 17, 1989

INVENTOR(S) : Brian Zdeb, Steve Pearson, Glenn L. Slater

It is certified that error appears in the above-identified patent and that said Letters Patent is hereby corrected as shown below:

In column 31, at line 49, delete "downstream and" and substitute --downstream end-- therefor.

Signed and Sealed this

Twenty-third Day of October, 1990

Attest:

HARRY F. MANBECK, JR.

*Attesting Officer*  *Commissioner of Patents and Trademarks*